(12) United States Patent
Iwasaka et al.

(10) Patent No.: US 7,169,105 B2
(45) Date of Patent: Jan. 30, 2007

(54) FLEXIBLE TUBE FOR AN ENDOSCOPE

(75) Inventors: Kikuo Iwasaka, Tokyo (JP); Tadashi Kasai, Tokyo (JP); Hideo Nanba, Tokyo (JP); Masaru Takeshige, Tokyo (JP); Akira Sugiyama, Tokyo (JP); Keiji Kunii, Tokyo (JP); Masanao Abe, Tokyo (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/822,651

(22) Filed: Apr. 13, 2004

(65) Prior Publication Data

US 2004/0193013 A1 Sep. 30, 2004

Related U.S. Application Data

(62) Division of application No. 09/848,301, filed on May 4, 2001, now Pat. No. 6,860,849.

(30) Foreign Application Priority Data

| May 8, 2000 | (JP) | ............................. 2000-134922 |
| May 15, 2000 | (JP) | ............................. 2000-142206 |
| May 26, 2000 | (JP) | ............................. 2000-156783 |

(51) Int. Cl.
*A61B 1/005* (2006.01)

(52) U.S. Cl. ....................................... 600/140; 600/139

(58) Field of Classification Search ................ 600/139, 600/140, 144; 138/145, 146, 149; 604/524–527
See application file for complete search history.

(56) References Cited

U.S. PATENT DOCUMENTS

| 4,283,447 A * | 8/1981 | Flynn .......................... 428/36.9 |
| 4,636,346 A * | 1/1987 | Gold et al. .................. 264/139 |
| 4,690,175 A | 9/1987 | Ouchi et al. |
| 4,753,222 A | 6/1988 | Morishita |
| 4,899,787 A | 2/1990 | Ouchi et al. |
| 5,125,913 A * | 6/1992 | Quackenbush .............. 604/264 |
| 5,217,002 A | 6/1993 | Katsurada et al. |
| 5,448,988 A * | 9/1995 | Watanabe .................... 600/139 |
| 5,533,985 A * | 7/1996 | Wang .......................... 604/264 |

(Continued)

FOREIGN PATENT DOCUMENTS

JP 2-283346 11/1990

(Continued)

*Primary Examiner*—John P. Leubecker
(74) *Attorney, Agent, or Firm*—Greenblum & Bernstein, P.L.C.

(57) ABSTRACT

A flexible tube for an endoscope has an elongated tubular core body, and an outer cover which is provided over the core body. The outer cover is composed of an inner layer, an outer layer and at least one intermediate layer. In this flexible tube, any one of the layers is different from one of the other layers in its property. Further, at least one of the layers has a thickness-varying region where the thickness of the layer varies in its longitudinal direction. In addition, the inner layer of the outer cover has projections which are integrally formed on the inner layer so that the projections project into holes and/or the recesses formed on the core body. This structure makes it possible to produce a flexible tube for an endoscope that has high durability, high flexibility and high chemical resistance as well as excellent operationability.

25 Claims, 15 Drawing Sheets

U.S. PATENT DOCUMENTS

| | | | |
|---|---|---|---|
| 5,536,235 A * | 7/1996 | Yabe et al. | 600/121 |
| 5,851,203 A * | 12/1998 | van Muiden | 604/525 |
| 5,860,963 A * | 1/1999 | Azam et al. | 604/528 |
| 5,876,331 A | 3/1999 | Wu et al. | |
| 5,885,207 A | 3/1999 | Iwasaaka | |
| 5,916,147 A | 6/1999 | Bourby | |
| 5,918,643 A * | 7/1999 | Roloff et al. | 138/137 |
| 5,938,653 A * | 8/1999 | Pepin | 604/527 |
| 6,083,152 A | 7/2000 | Strong | |
| 6,106,510 A * | 8/2000 | Lunn et al. | 604/525 |
| 6,197,014 B1 | 3/2001 | Samson et al. | |
| 6,206,824 B1 | 3/2001 | Ohara et al. | |
| 6,240,231 B1 * | 5/2001 | Ferrera et al. | 385/115 |
| 6,402,687 B1 | 6/2002 | Ouchi et al. | |
| 6,458,075 B1 | 10/2002 | Sugiyama et al. | |
| 6,599,239 B2 | 7/2003 | Hayakawa et al. | |
| 6,648,024 B2 * | 11/2003 | Wang | 138/177 |
| 2002/0032408 A1 * | 3/2002 | Parker et al. | 604/103.09 |
| 2003/0199836 A1 * | 10/2003 | Tiernan et al. | 604/264 |
| 2004/0064130 A1 * | 4/2004 | Carter | 604/523 |

FOREIGN PATENT DOCUMENTS

| | | |
|---|---|---|
| JP | 5-50287 | 7/1993 |
| JP | 6-98115 | 12/1994 |
| JP | 2641789 | 5/1997 |

* cited by examiner

FLEXIBLE TUBE FOR AN ENDOSCOPE

This application is a divisional of U.S. patent application Ser. No. 09/848,301, filed May 4, 2001 now U.S. Pat. No. 6,860,849, the disclosure of which is expressly incorporated herein by reference in its entirety.

BACKGROUND OF THE INVENTION

1. Field of the Invention

The present invention relates to a flexible tube for an endoscope.

2. Description of the Prior Art

Generally, a flexible tube for an endoscope has a structure which includes a tubular core obtained by covering the outer periphery of a spiral tube with a mesh tube and an outer cover formed of a synthetic resin or the like and provided over the outer periphery of the tubular core.

In endoscopic examination, the flexible tube for an endoscope is inserted along the body cavity to a deep part such as the stomach, duodenum, small intestine, and large intestine. In order to perform the inserting operation easily and reliably, it is necessary for the flexible tube that a push-in force applied to the proximal end (side closer to the operator) of the flexible tube is fully transmitted to its distal end. However, if bucking occurs in the flexible tube, the push-in force can not be fully transmitted to the distal end because the push-in force is partially absorbed by the bent part where the buckling occurs. This means that such a flexible tube for an endoscope can not achieve reliable inserting operation. In order to avoid the occurrence of such buckling, it is necessary for the flexible tube to have sufficient flexibility so that bending is hard to occur. Further, the outer cover must be firmly attached or bonded to the tubular core since buckling is liable to occur at areas where the outer cover is peeled off from the tubular core.

Furthermore, in order to perform the inserting operation reliably, it is also necessary for the flexible tube that a rotational force (that is, a twist) applied to the proximal end thereof is fully transmitted to the distal end thereof. In other word, a flexible tube for an endoscope is also required to have satisfactory rotational followability.

Moreover, a flexible tube for an endoscope is also required to have a relatively high stiffness on the proximal end side (side closer to the operator) and have a flexibility on the distal end side from the viewpoint of the operability and safety of insertion and reduction in the burden on the patient.

Up to now, there are known several flexible tubes for an endoscope which aim to improve the insertion operability in view of the problems described above. One of such flexible tubes is disclosed in Japanese Laid-open Patent Applications No. Hei 5-50287, in which an outer cover of a flexible tube for an endoscope is constructed from a double layer structure comprised of an outer layer made of a material having good elasticity and an inner layer made of a material having good resiliency, thereby improving resiliency of the flexible tube as a whole. Other example of such flexible tube is disclosed in Japanese Patent No. 2641789, in which a distal end side of the flexible tube is made of a soft elastomer and a proximal end side thereof is made of a hard elastomer so that the stiffness varies from the distal end side toward the proximal end side.

However, in these prior arts described in the above, the bonding force between the outer cover and the core has been left out of consideration, so that there is a case that the outer cover is peeled off from the core after repeated use, thus leading to the deterioration in flexibility and resistance to buckling of the flexible tube. In short, there is a problem in the durability of the flexible tube for an endoscope.

Furthermore, although an endoscope must be cleaned and disinfected every time when it is used, in the above prior arts no consideration is given to the chemical resistance of the outer covers. Consequently, in these prior arts, deterioration proceeds during the repeated disinfections, which results in possibility of generation of fine cracks or the like and peeling off of the outer cover from the core.

SUMMARY OF THE INVENTION

In view of the problems in the prior art described in the above, it is the object of the present invention to provide a flexible tube for an endoscope that possesses various kinds of performances required for a flexible tube for an endoscope, in particular to provide a flexible tube for an endoscope excellent in the operability of insertion, resistance to chemicals and durability.

In order to achieve the above object, the present invention is directed to a flexible tube for an endoscope, comprising:

an elongated tubular core body; and an outer cover which is provided over the core body, the outer cover having a portion which is formed into a laminate structure composed of at least three layers.

In this invention, it is preferred that the layers of the laminate structure include an inner layer, an outer layer and at least one intermediate layer formed between the inner layer and the outer layer.

Further, in this invention, it is also preferred that the core body has a plurality of holes and/or a plurality of recesses. In this case, it Is preferred that the core body includes: a coil that is formed by winding a band-shaped material into a spiral form; and a reticular tube that is formed by weaving a plurality of fine wires together, the reticular tube being provided over the coil. Further, it is also preferred that the inner layer of the outer cover has projections which are integrally formed on the inner layer so that the projections project into the holes and/or the recesses.

Furthermore, in this invention, it is also preferred that at least one of the fine wires forming the reticular tube is coated with a synthetic resin so that a coating of the synthetic resin is provided on the fine wire, in which at least a part of the coating is fused with and bonded to the inner layer of the outer cover.

Moreover, in this invention, it is also preferred that the inner layer of the outer cover contains a material having a compatibility with the synthetic resin of the coating.

Further, in this invention, it is also preferred that the portion of the laminate structure of the outer cover has a substantially uniform thickness over its entire region.

Furthermore, in this invention, it is also preferred that any one of the inner, outer and intermediate layers is different from one of the other layers in its physical property and/or chemical property.

Moreover, in this invention, it is also preferred that any one of the inner, outer and intermediate layers is different from one of the other layers in its hardness.

Moreover, in this invention, it is also preferred that the outer layer of the outer cover contains a material having resistance to chemical.

Moreover, in this invention, it is also preferred that the intermediate layer of the outer cover is formed of a material having higher elasticity than that of the outer layer.

Moreover, in this invention, it is also preferred that the outer layer of the outer cover is formed of a material having higher hardness than that of any one of the inner and intermediate layers.

Moreover, in this invention, it is also preferred that at least a part of the outer layer of the outer cover has higher hardness than that of any of the inner and intermediate layers.

Moreover, in this invention, it is also preferred that the intermediate layer of the outer cover is formed so as to function as cushioning means between the inner layer and the outer layer.

Moreover, in this invention, it is also preferred that at least one of the inner, outer and intermediate layers of the outer cover is formed of a material that contains at least one selected from the group consisting of polyurethane-based elastomer, polyester-based elastomer, polyolefine-based elastomer, polystyrene-based elastomer, polyamide-based elastomer, fluorine-based elastomer, and fluororubber.

Moreover, in this invention, it is also preferred that each of the inner, outer and intermediate layers of the outer cover is formed of a material that contains at least one selected from the group consisting of polyurethane-based elastomer, polyester-based elastomer, polyolefine-based elastomer, polystyrene-based elastomer, polyamide-based elastomer, fluorine-based elastomer, and fluororubber.

Further, in this invention, it is also preferred that the outer cover is provided over the core body through an extrusion molding process.

Furthermore, in this invention, it is also preferred that the flexible tube has tip and base ends, and flexibility of the flexible tube increases in a gradual or stepwise manner along the direction from the base end toward the tip end.

Moreover, in this invention, it is also preferred that any one of the layers constituting the portion of the laminate structure of the outer cover is different from one of the other layers in its physical property and/or chemical property.

Moreover, in this invention, it is also preferred that any one of layers constituting the laminate structure of the outer cover is different from one of the other layers in hardness.

Moreover, in this invention, it is also preferred that at least one of the layers constituting the portion of the laminate structure has a thickness-varying region where the thickness of the layer varies in its longitudinal direction.

In this case, it is preferred that the thickness-varying region extends substantially over an entire region of the layer, and within the thickness-varying region the thickness of the layer varies in its longitudinal direction in a gradual or stepwise manner.

Further, it is also preferred that the layer with the thickness-varying region has at least one uniform thickness region which is formed so as to adjoin the thickness-varying region.

Furthermore, it is also preferred that the layer having the thickness-varying region is formed of a material that is different from materials constituting the other layers in its hardness.

Moreover, it is also preferred that each of at least two of the layers constituting the portion of the laminate structure has a thickness-varying region where the thickness of the layer varies in its longitudinal direction.

Moreover, it is also preferred that the outer cover is provided over the core body through an extrusion molding process. In this case, it is preferred that in the extrusion molding process a constituent material for each of the layers is fed at a predetermined feeding rate while the core body is fed at a predetermined feeding speed, in which the thickness of the layer having the thickness-varying region is controlled by adjusting the feeding rate of the material for the layer during the extrusion molding process and/or adjusting the feeding speed of the core body during the extrusion molding process.

Further, in this invention, it is preferred that at least one of the layers constituting the portion of the laminate structure has at least two regions and at least one boundary part along its longitudinal direction, and one of the regions is contiguous to the other region through the boundary part, in which one of the regions is different from the other regions adjacent thereto in its physical property and/or chemical property.

In this case, it is preferred that one of the regions is formed of a material which is different from that forming the other region adjacent thereto.

Further, it is also preferred that each of at least two of the layers constituting the portion of the laminate structure has at least two regions and at least one boundary part along its longitudinal direction, and one of the regions is contiguous to the other region through the boundary part, in which one of the regions is different from the other region adjacent thereto in its physical property and/or chemical property. In this case, it is preferred that the outer cover is formed such that the boundary part of one layer is not located above or below the boundary part of the other layer in its thickness direction.

Furthermore, it is also preferred that the boundary part is formed as a property-varying part within which the physical property and/or the chemical property of the layer gradually vary in its longitudinal direction. In this case, the boundary part is formed of a mixture of a material constituting one of the regions and a material constituting the other region.

Moreover, it is also preferred that the layer having the boundary part is formed such that the physical property and/or the chemical property within the boundary part vary in its longitudinal direction in a substantially stepwise manner.

Moreover, it is also preferred that in the layer having the at least two regions, one of the regions is different from the other region adjacent thereto in its hardness.

Moreover, it is also preferred that the flexible tube has tip and base ends, and flexibility of the flexible tube increases in a gradual or stepwise manner along the direction from the base end to the tip end.

These and other objects, structures and advantages of the present invention will be apparent more clearly from the following description of the invention based on the examples.

DETAILED DESCRIPTION OF THE PREFERRED EMBODIMENTS

Hereinafter, detailed description of the preferred embodiments of a flexible tube for an endoscope according to the present invention will be given with reference to the appended drawings.

I. First Embodiment (Flexible Tube 1A)

(I-1) Overall-Structure of Electronic Endoscope

Figure 1:
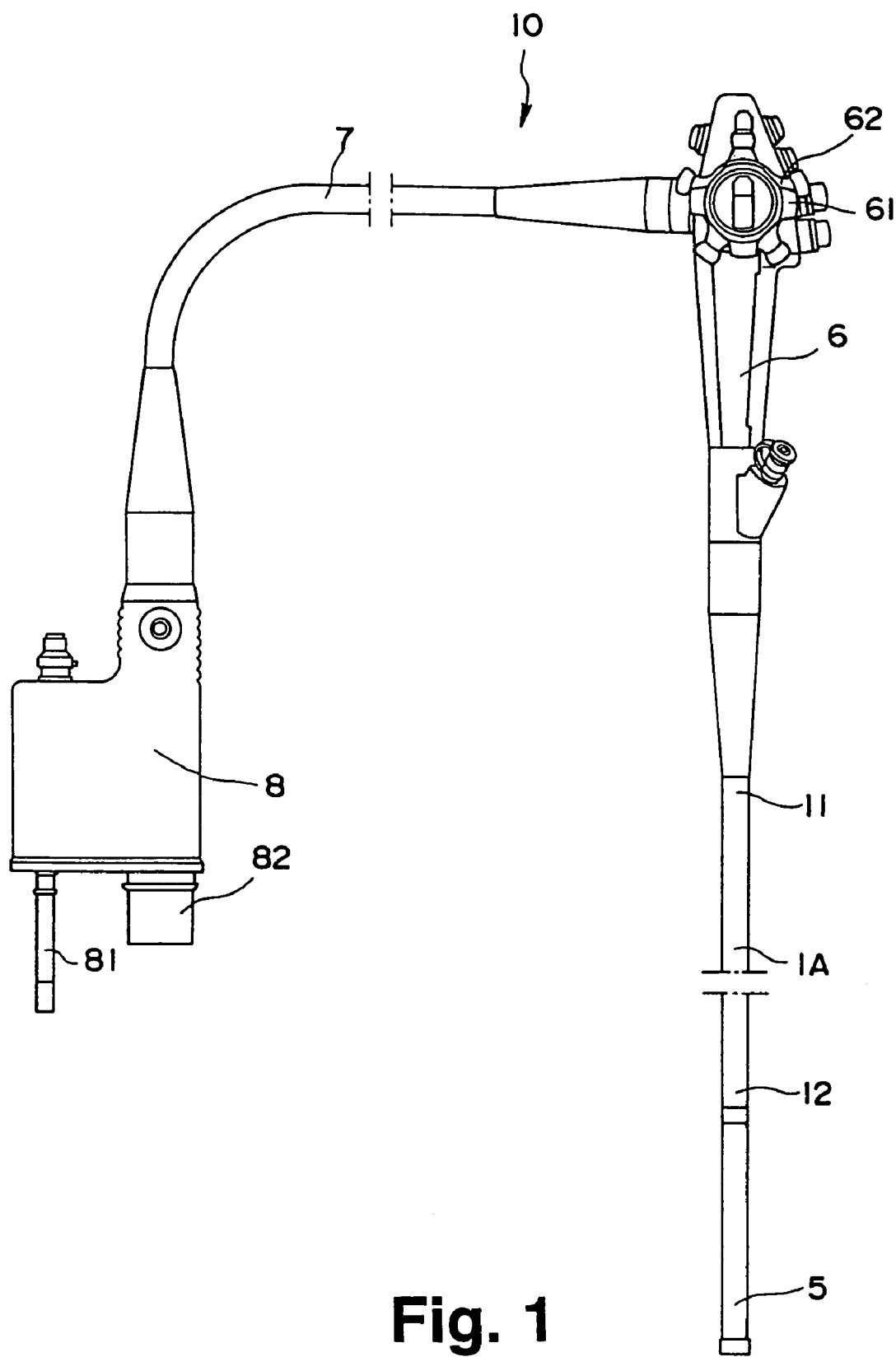
FIG. 1 shows an overall structure of an endoscope having a first embodiment of a flexible tube according to the present invention.
Figure 2:
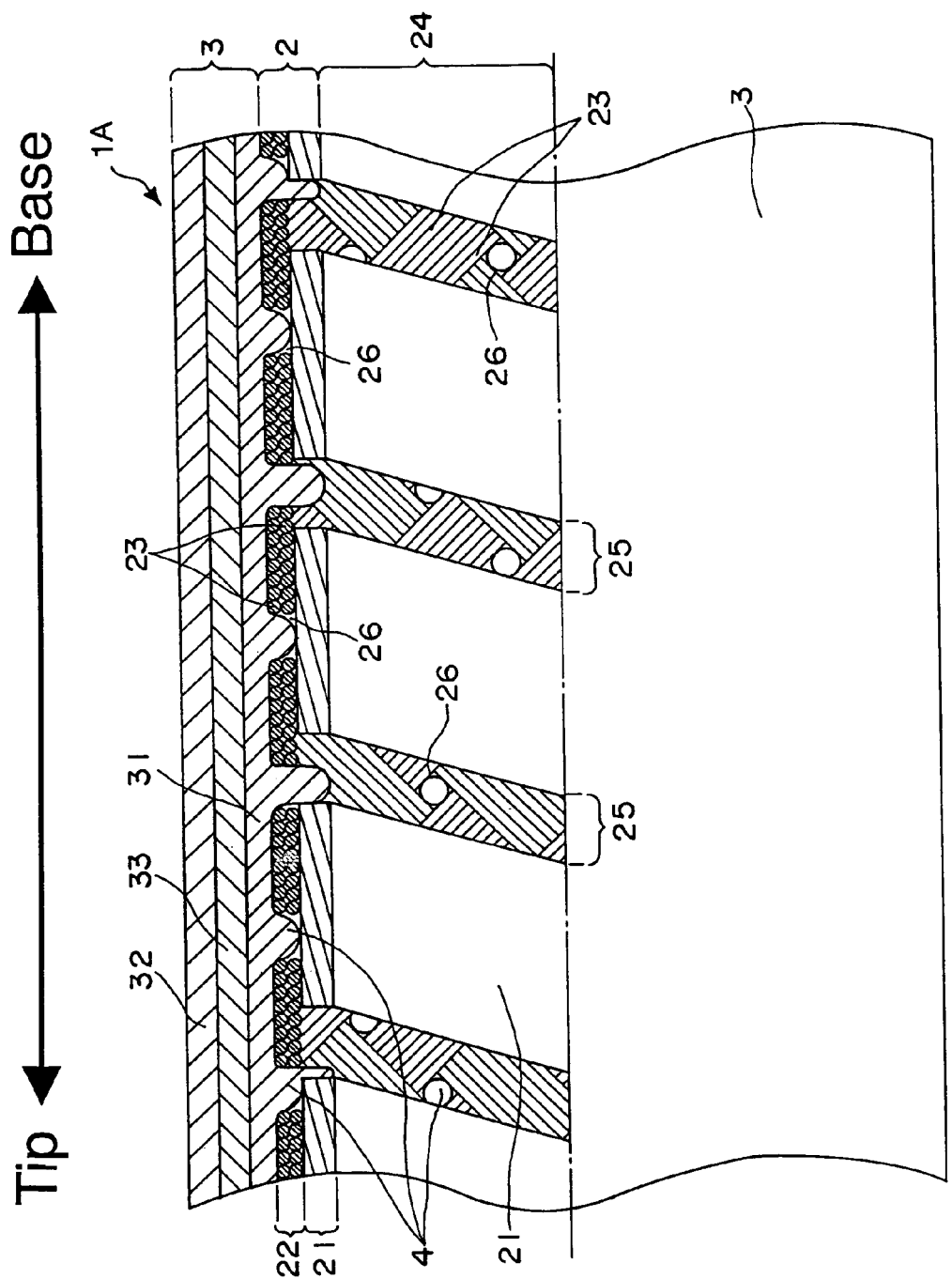
FIG. 2 is a sectional view which shows a part of the flexible tube in FIG. 1.

First, a first embodiment of the flexible tube for an endoscope will be described-with reference to FIGS. 1 and 2. FIG. 1 shows an overall structure of an electronic endoscope 10 (electronic scope) having a flexible tube 1A according to the present invention. FIG. 2 is a sectional view which shows a part of the flexible tube 1A of the electronic endoscope 10 in FIG. 1. In FIG. 2, the right-hand side corresponds to the base side (i.e., side closer to an operator), and the left-hand side corresponds to the tip side of the electronic endoscope 10.

In the following, the upper side and the lower side in FIG. 1 will be referred to as "base" and "tip," respectively. Further, the electronic endoscope will be referred to simply as an "endoscope." Furthermore, the flexible tube for an endoscope will be referred to simply as a "flexible tube."

As shown in FIG. 1, the endoscope 10 has an elongated flexible tube (insertion section) 1A designed to be inserted into a body cavity of a living body; a bendable tube 5 provided on a tip end 12 of the flexible tube 1A; an operating section 6 provided on a base end 11 of the flexible tube 1A, which is gripped by an operator during an endoscopic examination to manipulate the endoscope 10; a light guide flexible tube 7 connected at one end thereof to the operating section 6; and a plug 8 provided on the other end of the light guide flexible tube 7.

On the side faces of the operating section 6, there are provided operating knobs 61 and 62. When changing the direction of the bendable tube 5 during the endoscopic examination, the operator turns each of the operating knobs 61 and 62 to pull appropriately wires (not shown) arranged in the flexible tube 1A. In this way, the bendable tube 5 is bent to a desired direction.

The endoscope 10 has an imaging element (CCD) for taking an image of an observation area, which is provided at the tip end of the bendable tube 5. Further, the endoscope 10 has a connector 82 provided on one end of the plug 8. The connector 82 is connected to a light source device which is connected to a monitor (not shown) via a cable.

In the endoscope 10, the reflected light (which forms an image of the observation area) from the observation area is received by the imaging element. Then, the imaging element outputs an image signal corresponding to the image formed on the imaging element by the reflected light. The image signal is transmitted to the plug 8 via an image signal cable (not shown in the drawing) which extends inside the bendable tube 5, the flexible tube 1A, the operating section 6 and the light guide flexible tube 7. Then, in the light source device, the image signal is subjected to predetermined processing (such as signal processing, image processing, and the like), and then the processed signal is sent to the monitor. In this way, an image (electronic image) taken by the imaging element is displayed on the screen of the monitor.

In the above, the description was given for the case where a flexible tube for an endoscope according to the present invention is applied to an electronic endoscope (electronic type endoscope). However, it is to be noted that a flexible tube of this invention may also be applied to a fiberscope (optical type endoscope).

As shown in FIG. 2, the flexible tube 1A has a core body (structural body) 2 and an outer cover 3 that covers an outer periphery of the core body 2. Further, inside the flexible tube 1A, there is formed a hollow space 24 through which internal elements (such as optical fibers, cables, operation wires, tubular elements, and the like) can be passed.

The core body 2 acts as a reinforcing member for reinforcing the flexible tube 1A, and also acts as a protecting member for protecting the internal elements described above. This core body 2 is constructed from a coil 21 and a reticular tube 22 which covers the outer periphery of the coil 21, so that the core body 2 has an elongated tubular shape. By constructing the core body 2 using the coil 21 and the reticular tube 22, it becomes possible to give the flexible tube 1 torque transmission ability, tracking ability to a body cavity (i.e., bendability), and sufficient mechanical strength.

The coil 21 is formed from a flat metal band. Specifically, this coil 21 is formed by winding the metal band into a spiral form so as to have a uniform diameter with a gap 25 between the adjacent windings. Preferred examples of materials which may be used for the metal band include stainless steel, copper alloys, and the like.

The reticular tube 22 is formed by weaving a plurality of bundles of fine metal wires 23 in a lattice manner so as to have spaces 26 there between as shown in FIG. 2. Each of the bundles is formed by arranging a plurality of fine wires side by side. This reticular tube 22 may be formed from nonmetal fibers. Preferred examples of materials which may be used for the fine metal wires 23 include stainless steel, copper alloys and the like. In this invention, it is preferred that at least one of the fine wires (or fibers) constituting the reticular tube 22 is coated with a synthetic resin so that a coating of the synthetic resin is provided thereon.

On the outer periphery of the reticular tube 22, each of the spaces 26 of the reticular tube 22 forms either a recess or hole of the core body 2 depending on its location with respect to the coil 21. Specifically, as shown in FIG. 2, some of the spaces 26 located on the metal band of the coil 21 form recesses of the core body 2, while the other spaces 26 located on the gaps 25 between the adjacent windings form holes of the core body 2. As a result of the structure described above, the core body 2 has a plurality of recesses and holes.

The outer periphery of the core body 2 is covered with the outer cover 3. This outer cover 3 or a portion of the outer cover 3 is formed into a laminate structure which is composed of inner, outer and intermediate layers 31–33.

As will be described below, one of the inner, outer and intermediate layers 31–33 of the outer cover 3 is formed of a material which is different from a material constituting one of the other layers in its physical property or chemical property. Examples of such physical property include stiffness, flexibility, hardness, elongation rate, tensile strength, shearing strength, bending strength and the like. Further, examples of such chemical property include chemical resistance, weather resistance and the like.

(I-2) Inner Layer of Outer Cover

The inner layer 31 of the outer cover 3 is formed on the innermost side of the outer cover 3, and it adheres to the core body 2. Physical property of the inner layer 31 is substantially homogeneous over its entire region.

On the inner peripheral surface of the inner layer 31, as shown in FIG. 2, there are integrally formed a plurality of projections (anchoring projections) 4. Respective projections 4 project into spaces 26 of the core body 2 (i.e., holes and recesses of the core body 2). As shown in FIG. 2, in the recesses (spaces 26) of the core body 2, each of the projections 4 extends to the outer periphery of the coil 21. Further, in the holes (spaces 26) of the core body 2, each of the projections 4 extends into the gap 25 of the coil 21.

In this invention, it is preferable that the inner layer 31 is made of a material by which formation of the projections 4 can be controlled appropriately, so that appropriate number of projections 4 having appropriate size and shape can be integrally formed on the inner layer 31 as shown in FIG. 2.

By forming the projections 4 as described above, engagements between the projections 4 and the recesses of the core body 2 and between the projections 4 and the holes of the core body 2 are achieved, and therefore the outer cover 3 is firmly fixed with respect to the core body 2 by anchoring effect given by the engagements. Such anchoring effect enables the outer cover 3 to expand and contract sufficiently in conformity with the bending of the core body 2. Further, due to the anchoring effect, it is possible to maintain a state that the outer cover 3 adheres to the core body 2 even when the flexible tube 1A is bended. Therefore, by forming the flexible tube in this way, it is possible to give high flexibility to the flexible tube.

Further, the bonding strength between the outer cover 3 and the reticular tube 22 is enhanced by the formation of the projections 4, so that the peeling off of the outer cover 3 from the reticular tube 22 is prevented even after repeated use of the endoscope. This means that the flexible tube 1A of this invention can maintain high flexibility even after the endoscope is repeatedly used, that is, the flexible tube has excellent durability.

Further, when the coating of the synthetic resin is given to at least one of the fine wires 23 forming the reticular tube 22 as described above, at least a part of the applied coating (synthetic resin) is fused with and is bonded to the inner layer 31, thereby providing strong bonding therebetween. In this case, in order to enhance the boding strength between the fine wires 23 and the inner layer 31, it is preferable that the inner layer 31 of the outer cover 3 contains a material that has a compatibility with the synthetic resin of the coating.

By using the reticular tube 22 formed from the fine wires with the coating of the synthetic resin as described above, a higher adhesion between the outer cover 3 and the core body 2 is realized. Therefore, by providing the outer cover 3 on the core body 2 having the reticular tube 22 with the coating of the synthetic resin and by forming the projections 4 on the inner layer 31 as described above, it becomes possible to obtain a flexible tube having high flexibility and high durability. In this connection, it is to be noted this excellent ability is given by the effect of the coating of the synthetic resin provided on the fine wire(s) as well as the effect of the projections 4 described above.

In this invention, a constituent material for the inner layer 31 is not particularly limited. Examples of such material include various resins having elasticity such as polyvinyl chloride, polyolefine (e.g., polyethylene, polypropylene, ethylene-vinylacetate copolymer and the like), polyamide, polyester (e.g., polyethylene terephthalate (PET), polybutylene terephthalate and the like), polyurethane, polystyrene resin, fluoro-based resin (e.g., polytetrafluoroethylene, ethylene-tetrafluoroethylene copolymer and the like), polyimide, and the like; and various elastomers such as polyurethane-based elastomer, polyester-based elastomer, polyolefine-based elastomer, polyamide-based elastomer, polystyrene-based elastomer, fluorine-based elastomer, silicone rubber, fluororubber, latex rubber, and the like. These can be used alone or as a mixture of two or more thereof. In this invention, a material containing at least one of polyurethane-based elastomer, polyolefin-based elastomer, and polyester-based elastomer is preferably used to form the inner layer 31, since they can be easily formed into the inner layer with the projections 4 as shown in FIG. 2.

The average thickness of the inner layer 31 (excluding the portions of the projections 4) is not particularly limited, but the thickness is preferably in the range of 0.05 to 0.8 mm, and more preferably in the range of 0.05 to 0.4 mm.

(I-3) Outer Layer of Outer Cover

The outer layer 32 is formed on the outermost side of the outer cover 3, and has almost homogeneous physical properties over its entire region. In this invention, it is preferable that the outer layer 32 is formed of a material having a resistance to chemicals. By using such a material, it is possible to suppress the degradation of the outer cover 3 due to repeated cleaning and disinfection. Further, it is also possible to suppress deterioration in flexibility caused by the hardening of the outer cover due to repeated cleaning and disinfection. In addition, it is also possible to prevent peeling off of the outer cover 3 from the reticular tube 22 due to cracks or the like caused by repeated cleaning and disinfection.

The outer layer 32 is formed so as to have a relatively high hardness. This prevents the generation of scratches that are liable to produce cracks or the like on the surface of the outer cover 3. In this invention, it is preferable that the outer layer 32 of the outer cover 33 has higher hardness than that of any one of the inner and intermediate layers 31 and 33 in part or over its entire region.

In this invention, a constituent material for the outer layer 32 is not particularly limited. Examples of such material include various resins having elasticity such as polyvinyl chloride, polyolefine (e.g., polyethylene, polypropylene, ethylene-vinylacetate copolymer and the like), polyamide, polyester (e.g., polyethylene terephthalate (PET), polybutylene terephthalate and the like), polyurethane, polystyrene resin, fluoro-based resin (e.g., polytetrafluoroethylene, ethylene-tetrafluoroethylene copolymer and the like), polyimide, and the like; and various elastomers such as polyurethane-based elastomer, polyester-based elastomer, polyolefine-based elastomer, polyamide-based elastomer, polystyrene-based elastomer, fluorine-based elastomer, silicone rubber, fluororubber, latex rubber, and the like. These can be used alone or as a mixture of two or more thereof. In this invention, a material containing at least one of polyolefine (e.g., ethylene-vinylacetate copolymer and the like), fluoro-based resin (e.g., polytetrafluoroethylene, ethylene-tetrafluoroethylene copolymer and the like), polyester-based elastomer, polyolefine-based elastomer, fluorine-based elastomer, silicone rubber and fluororubber is preferably used to form the outer layer 32, since they have high resistance to chemical.

The thickness of the outer layer 32 is not particularly limited, but the thickness is preferably in the range of 0.05 to 0.8 mm, and more preferably in the range of 0.05 to 0.4 mm.

(I-4) Intermediate Layer of Outer Cover

In this invention, it is preferable that the intermediate layer 33 has a higher elasticity than that of the outer layer 32, and more preferably the intermediate layer 33 has a higher elasticity than that of any one of the inner and outer layers 31 and 32. With this arrangement, the intermediate layer 33 functions as a cushioning layer (cushioning means) between the inner layer 31 and the outer layer 32. (In the following, such a function of the intermediate layer 33 is referred to as "cushioning function.") Accordingly, by forming the intermediate layer 33 as described above, it is possible to give higher flexibility to the flexible tube.

Hereinafter, the cushioning function of the intermediate layer 33 is described in more detail. When the flexible tube 1A is bent by an external force, the high elastic force is generated in the bent intermediate layer 33 through the deformation thereof. The generated elastic force is transmitted effectively to the inner layer 31 and the outer layer 32, respectively, since the intermediate layer 33 is sandwiched between the inner layer 31 and the outer layer 32 each of which has relatively low elasticity. When the external force has been removed, the bent flexible tube 1A is restored to its original shape by the high elastic force generated in the bent intermediate layer 33. In this connection, it is to be noted that the restoration of the flexible tube into its original shape is achieved by the cushioning function of the intermediate layer 33, and that such a cushioning function gives the flexible tube high flexibility.

In this invention, a constituent material for the intermediate layer 33 is not particularly limited. Examples of such material include various resins having elasticity such as polyvinyl chloride, polyolefine (e.g., polyethylene, polypropylene, ethylene-vinylacetate copolymer), polyamide, polyester (e.g., polyethylene terephthalate (PET), polybutylene terephthalate), polyurethane, polystyrene resin, fluoro-based resin (e.g., polytetrafluoroethylene, ethylene-tetrafluoroethylene copolymer), polyimide, and the like; and various elastomers such as polyurethane-based elastomer, polyester-based elastomer, polyolefine-based elastomer, polyamide-based elastomer, polystyrene-based elastomer, fluorine-based elastomer, silicone rubber, fluororubber, latex rubber, and the like. These can be used alone or as a mixture of two or more thereof. In this invention, a material containing at least one of low hardness polyurethane-based elastomer, low hardness polyolefin-based elastomer, and low hardness polyester-based elastomer is preferably used to form the intermediate layer 33, since such elastomers have high elasticity.

Although the intermediate layer 33 in this embodiment is given a single layer structure, it may be given a structure of two or more layers.

The average thickness of the intermediate layer 33 is not particularly limited, but the average thickness is preferably in the range of 0.05 to 0.8 mm, and more preferably in the range of 0.05 to 0.4 mm.

(I-5) Outer Cover Having the Layers

In this invention, the average thickness of the outer cover 3 (excluding the portions of the projections 4) is not particularly limited, as long as the outer cover 3 can protect the core body 2 and the internal elements arranged in the core body 2 from a fluid (e.g., body fluid) and it does not impair the bendability of the flexible tube. However, the average thickness of the outer cover 3 (excluding the portions of the projections 4) is preferably in the range of 0.15 to 0.9 mm, and more preferably in the range of 0.3 to 0.8 mm.

In addition, it is preferable that the outer cover 3 (excluding the portions of the projections 4) has a substantially uniform-thickness over its entire region. With this arrangement, it is possible to produce a flexible tube having a substantially uniform diameter over its entire region. When an endoscope having a flexible tube with such an outer cover is used in an endoscopic examination, it is possible for an operator to easily and smoothly insert the insertion section (flexible tube) of the endoscope into a body cavity of a patient, thus making it possible to reduce the burden on the patient during the endoscopic examination.

(I-6) Manufacturing Method of Flexible Tube

A method of manufacturing a flexible tube for an endoscope as described in the above is not particularly limited, but it is preferable that the flexible tube of this invention is manufactured by extrusion molding. When such extrusion molding is performed using an extrusion molding machine equipped with a plurality of extrusion ports, it is possible to extrude the inner, outer and intermediate layers 31–33 simultaneously so that the core body 2 is covered with the outer cover 3 having the laminate structure composed of these layers. In this extrusion molding, it is preferable to adjust the feeding amount (i.e., feeding amount per unit time) of constituent material for each layer from each extrusion port while adjusting the feeding speed of the core body 2. This method makes it is possible to control properly the thickness, shape and property of each layer.

The temperature of the material when performing the extrusion molding is not particularly limited, but the temperature is preferably about 130 to 220° C., and more preferably about 165 to 205° C. Within such a range, the material has an excellent moldability. Therefore, by performing the extrusion molding using the material whose temperature is within the range described above, it becomes possible to improve uniformity of the thickness of the outer cover 3 provided on the core body 2.

II. EXAMPLES OF FIRST EMBODIMENT

Next, specific examples of the first embodiment of the present invention will be described below.

1. Preparation of Flexible Tube for an Endoscope

Example 1a

First, a coil 21 having an outer diameter of 9.9 mm and an inner diameter of 9.6 mm was prepared by winding a band-shaped stainless steel material having a width of 3 mm. Next, stainless steel fine wires 23 at least one of which had been given a coating of a polyamide resin and each of which had a diameter of 0.1 mm were prepared, and then using these fine wires a plurality of bundles of ten fine wires were prepared. These bundles of the ten fine wires 23 were woven together in a lattice manner to obtain a reticular tube 22. Then, the obtained reticular tube 22 was provided on the prepared coil 21 so that the outer periphery of the coil 21 was covered with the reticular tube 22. In this way, a core body 2 was prepared.

Next, using an extrusion-molding machine, an outer cover 3 composed of inner, outer and intermediate layers 31–33 was provided on the outer periphery of the core body 2 so that the core body 2 was covered with the outer cover 3. In this way, a flexible tube for an endoscope with a length of 1.6 m was prepared. In this connection, it is to be noted that the length of 1.6 m means the length of an available (effective) portion of the flexible tube that can be used for a flexible tube for an endoscope, that is the length of 1.6 m means an available (effective) length of the flexible tube. Therefore, the actually prepared flexible tube had a length more than 1.6 m by including additional portions at the both ends of the available portion of the flexible tube. In this regard, however, it goes without saying that the available length is not limited to 1.6 m mentioned above.

A constituent material used for each of the layers in this Example is shown in the attached Table 1. In addition, the thickness of each of the layers is also shown in Table 1.

Example 1b

A flexible tube for an endoscope was prepared in the same manner as in Example 1a except that the thickness of the inner layer 31 was changed as shown in the attached Table 1.

Example 1c

A flexible tube for an endoscope was prepared in the same manner as in Example 1a except that the thickness of the intermediate layer 33 was changed as shown in the attached Table 1.

Example 1d

A flexible tube for an endoscope was prepared in the same manner as in Example 1a except that the thickness of the outer layer 32 and the material for the outer layer 32 were changed as shown in the attached Table 1.

Example 1e

A flexible tube for an endoscope was prepared in the same manner as in Example 1a except that the material for the outer layer 32 was changed as shown in the attached Table 1.

Comparative Example 1a

A core body 2 was prepared in the same manner as in Example 1a. Then, using an extrusion-molding machine, an outer cover 3 composed of inner and outer layers 31 and 32 was provided on the outer periphery of the core body 2 so that the core body 2 was covered with the outer cover 3. In this way, a flexible tube for an endoscope with a length of 1.6 m was prepared. A constituent material for each layer of the outer cover 3 and the thickness of each layer are shown in the attached Table 1.

Comparative Example 1b

A flexible tube for an endoscope was prepared in the same manner as in Comparative Example 1a except that the material for the outer layer 32 was changed as shown in the attached Table 1.

Comparative Example 1c

A flexible tube for an endoscope was prepared in the same manner as in Example 1a except that the thickness of each of inner and outer layers 31 and 32 and the material for each of the inner and outer layers 31 and 32 were changed as shown in the attached Table 1.

Comparative Example 1d

A flexible tube for an endoscope was prepared in the same manner as in Example 1a except that the material for each of inner and outer layers 31 and 32 was changed as shown in the attached Table 1.

2. Observation of the Prepared Flexible Tubes

An observation of the cross-section of the outer cover was carried out for each of the flexible tubes of Examples 1a–1e and Comparative Examples 1a–1d. Through the observation, formation of projections 4 as shown in FIG. 2 was observed in each of the flexible tubes of Examples 1a–1e and Comparative Examples 1a, 1b and 1d, but no formation of projections 4 was observed in the flexible tube of Comparative Example 1c.

3. Evaluation of Flexible Tube (3-1) Chemical Resistance Test

A chemical resistance test was carried out for each of the flexible tubes of Example 1a–1e and Comparative Example 1a–1d. In this test, 100 L of 10% aqueous solution of iodine held at 25° C. was prepared first, and then each of the prepared flexible tubes was immersed in the aqueous solution for 200 hours. Then, the condition of each flexible tube was evaluated in accordance with the four rankings A–D given below.

Rank A:
 No Change in the Appearance; and
 No Occurrence of Cracks and Blisters in Outer Cover.
Rank B:
 Slight Change in the Appearance; and
 Occurrence of Blisters at a Few Spots of Outer Cover.
Rank C:
 Large Change in the Appearance; and
 Occurrence of Blisters at Many Spots of Outer Cover.
Rank D:
 Extremely Large Change in the Appearance; and
 Occurrence of a Large Number of Cracks and Blisters on Outer Cover.

The evaluation results in this test are shown in the attached Table 1.

(3-2) Flexibility Test

A flexibility test was carried out for each of the flexible tubes of Example 1a–1e and Comparative Example 1a–1d. In this test, the flexible tube for an endoscope supported at its both ends was subjected to bending by 90°, and the flexibility in that state was evaluated in accordance with the four rankings A–D given below.

Rank A:
 High Flexibility
 (A flexible tube of Rank A is considered to be best suited for use as a flexible tube for an endoscope.)
Rank B:
 Normal Flexibility
 (A flexible tube of Rank B is considered to be suited for use as a flexible tube for an endoscope.)
Rank C:
 Low Flexibility
 (A flexible tube of Rank C is considered to have problems in use as a flexible tube for an endoscope.)
Rank D:
 Almost No Flexibility
 (A flexible tube of Rank D is considered to be unsuited for use as a flexible tube for an endoscope.)

The result of the flexibility test is shown in the attached Table 1.

(3-3) Durability Test

A durability test was carried out for each of the flexible tubes of Examples 1a–1e and Comparative Examples 1a–1d. In the durability test, each of the flexible tubes was set to a state where the flexible tube was supported at its both ends, and in this state the operation of bending by 90° was repeated 300 times. Then, the degree of change in the flexibility after the repeated operation of bending was examined to evaluate the durability of each flexible tube in accordance with the four rankings A–D given below.

Rank A:
 Almost No Change in Flexibility
 (A flexible tube of Rank A is considered to have extremely high durability.)
Rank B:
 Slight Lowering of Flexibility (A flexible tube of Rank B is considered to have high durability.)
Rank C:
 Large Lowering of Flexibility (A flexible tube of Rank C is considered to have problems in its durability.)
Rank D:
 Extremely Large Lowering of Flexibility; and
 Occurrence of cracks and the like at many spots of the outer cover.
 (A flexible tube of Rank D is considered to be unsuited for use as a flexible tube for an endoscope.)

The result of the durability test is shown in the attached Table 1.

(3-4) Evaluation

The results in the attached Table 1 show that the flexible tube according to the present invention (i.e., Examples 1a–1e) has high chemical resistance and high flexibility as well as high durability. Further, the results in Table 1 also show that conventional flexible tubes (i.e., Comparative Examples 1a–1d) have some drawbacks.

Specifically, the flexible tube of Comparative Example 1a has poor resistance to chemical. This drawback is considered to result from the fact that the outer layer 32 of the outer cover 3 was made of the material with poor chemical resistance. Further, the flexible tube of Comparative Example 1b has poor flexibility. This drawback is considered to result from the fact that both the inner and outer layers 31 and 32 were formed of the materials with relatively high hardness. Furthermore, the flexible tube of Comparative Example 1c has poor flexibility and poor durability. These drawbacks are considered to result from the fact that no projections 4 as shown in FIG. 2 were formed on the inner layer 31. In addition, the flexible tube of Comparative Example 1d has poor durability. This drawback is considered to result from the fact that the inner layer 31 was formed of the material with relatively low hardness and therefore the projections 4 on the inner layer 31 had poor strength.

According to the present invention described above, appropriate materials that are suitable for each of layers of an outer cover 3 are used for preparing an outer cover 3, and the outer cover 3 is provided onto the core body 2 so that each of the layers has appropriate thickness and shape. This structure and the selection of material make it possible to provide a flexible tube for an endoscope that has high durability and high flexibility as well as high chemical resistance.

Further, when a material with high elasticity is used for the intermediate layer of the outer cover, it is possible to give higher flexibility to the flexible tube. In addition, when a material having a high adhesion with the core body is used for the inner layer of the outer cover, it is also possible to give high durability to the flexible tube for an endoscope.

III. Second Embodiment (Flexible Tube 1B)

Figure 3:
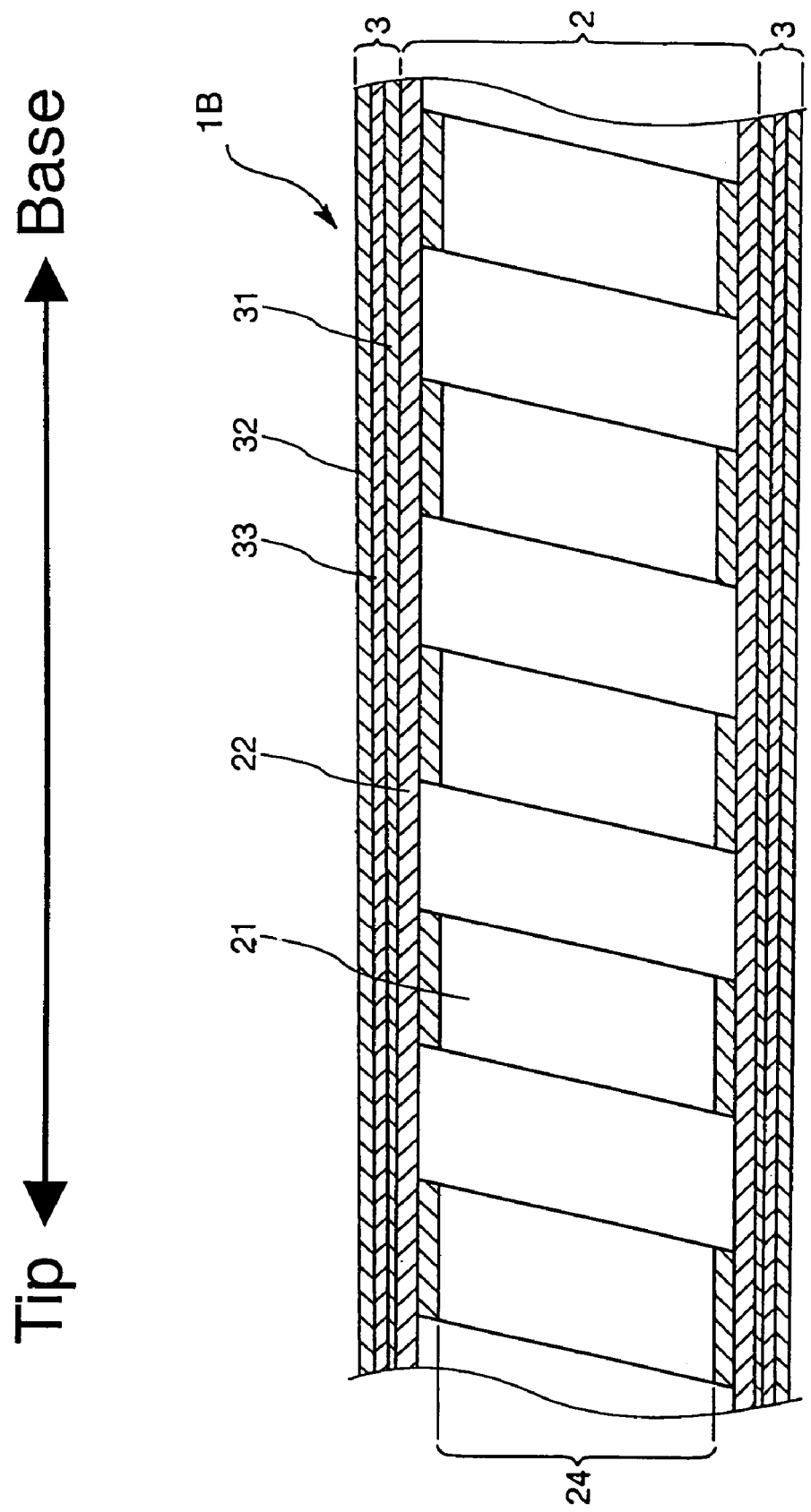
FIG. 3 is a sectional view which shows a part of a second embodiment of the flexible tube according to the present invention.

Next, a second embodiment of the flexible tube for an endoscope will be described with reference to FIG. 3. FIG. 3 is a sectional view which shows a part of a flexible tube 1B according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1. In the following, description of the configurations and features that are the same as those in the above-mentioned first embodiment will be omitted, and description will be given mainly with respect to the configurations and features that are different from those of the first embodiment.

As shown in FIG. 3, an outer cover (or a portion of the outer cover) 3 of the flexible tube 1B has a laminate structure which is composed of inner, outer and intermediate layers 31–33. The inner layer 31 has a smaller thickness at a portion nearer to the tip end 12 of the flexible tube 1B, while each of the outer and inner layers 32 and 33 has a substantially uniform thickness over its entire region. This structure gives the outer cover 3 a stiffness (e.g., bending stiffness) that decreases in the longitudinal direction from the base end 11 toward the tip end 12. By forming the outer cover 3 such that its stiffness varies in the longitudinal direction, it is possible to give a flexible tube flexibility that increases in the longitudinal direction from the base end 11 toward the tip end 12. According to such a flexible tube for an endoscope, since the flexible tube has a higher stiffness in a portion closer to the base end 11, it is possible to fully transmit to the tip end 12 the push-in force and the rotational force applied by the operator. On the other hand, since the flexible tube has high flexibility in a portion closer to the tip end 12, it is also possible to smoothly insert an insertion section (flexible tube) of an endoscope into an internal curved portion of a patient in a safe manner. Therefore, the flexible tube 1B as described above makes it possible for an operator to insert the insertion section with easy manipulation, thus enabling the reduction of the burden on the patient during the endoscopic examination.

In this embodiment, the rate of change in the thickness of the inner layer 31 in the longitudinal direction, that is, the shape of the inner layer 31 is appropriately determined to realize the desired rate of change in the stiffness of the flexible tube in the longitudinal direction. This makes it possible, for example, to produce various kinds of flexible tubes for an endoscope taking into account various shapes of internal portions of a living body, operator's tastes and the like.

Further, in this embodiment, the value of $T1_{min}/T1_{max}$ is not particularly limited, where the value of "$T1_{min}$" is given by the thickness of the thinnest part of the inner layer 31, and the value of "$T1_{max}$" is given by the thickness of the thickest part of the inner layer 31. However, the value of $T1_{min}/T1_{max}$ is preferably in the range of 0.05 to 0.95, and more preferably in the range of 0.1 to 0.6.

IV. Third Embodiment (Flexible Tube 1C)

Figure 4:
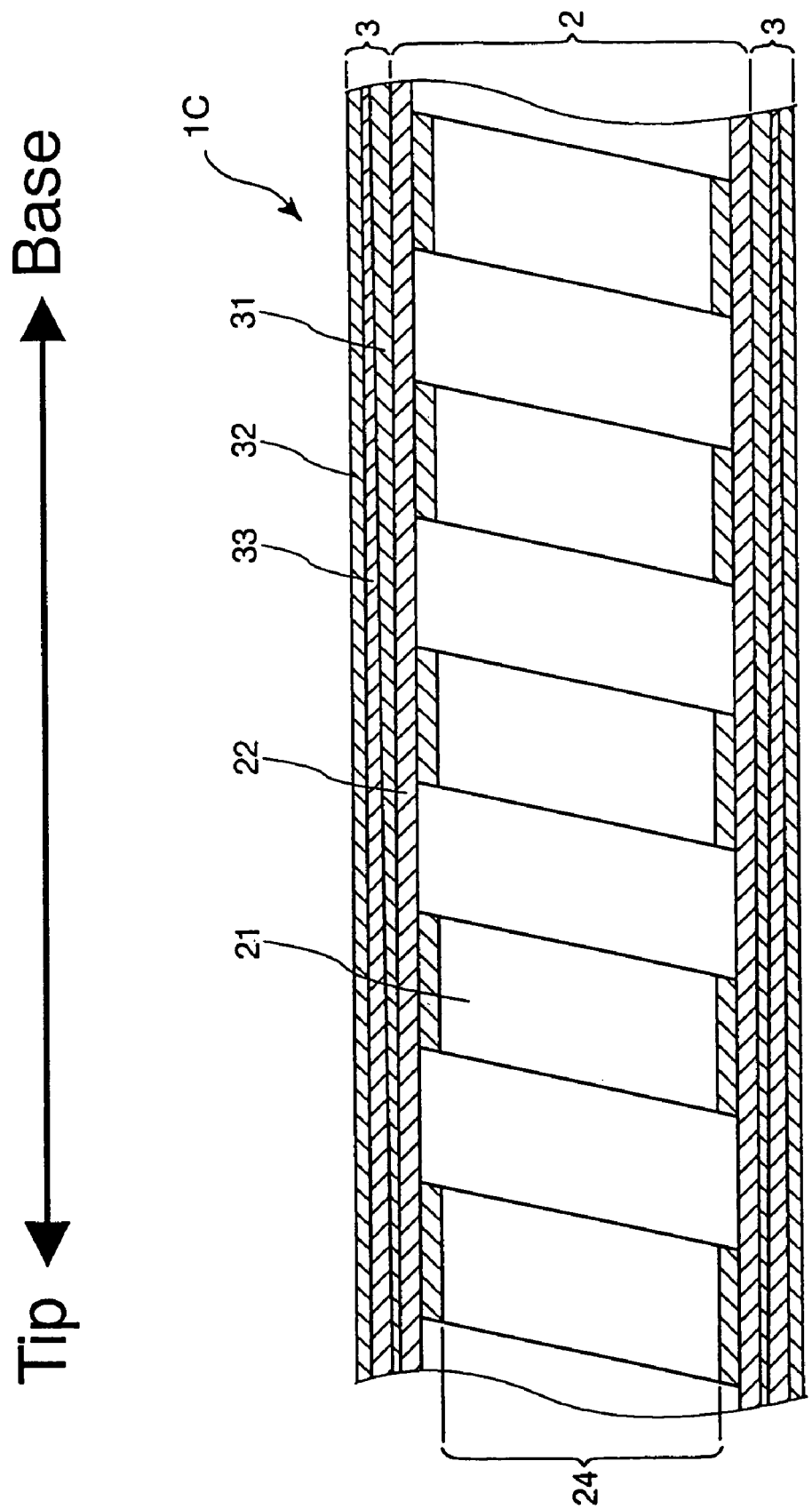
FIG. 4 is a sectional view which shows a part of a third embodiment of the flexible tube according to the present invention.

Next, a third embodiment of the flexible tube for an endoscope will be described with reference to FIG. 4. FIG. 4 is a sectional view which shows a part of a flexible tube 1C according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1.

In this embodiment, an outer cover 3 of the flexible tube 1C has a laminate structure composed of inner, outer and intermediate layers 31–33. Each of the inner and intermediate layers 31 and 33 has a thickness which gradually varies over its entire region; and the outer layer 32 has a substantially uniform thickness over its entire region.

As shown in FIG. 4, the thickness of the inner layer 31 gradually "decreases" in the direction from the base end 11 toward the tip end 12. Conversely, the thickness of the intermediate layer 33 gradually "increases" in the direction from the base end 11 toward the tip end 12. In this embodiment, the intermediate layer 33 is formed of a material having higher elasticity than that of the inner layer 31.

In this connection, it is to be noted that the thickness of the intermediate layer 33 decreases in the opposite direction to that of the inner layer 31. Further, it is also to be noted that the total thickness of the inner and intermediate layers 31 and 33 remains substantially uniform over the entire region of the outer cover 3, and the thickness of the outer cover 3 remains substantially uniform over its entire region, in spite of the fact that the thickness of each of the inner and intermediate layers 31 and 33 varies over its entire region.

In this embodiment, the value of $T3_{min}/T3_{max}$ is not particularly limited, where the value of "$T3_{min}$" is given by the thickness of the thinnest part of the intermediate layer 33, and the value of "$T3_{max}$" is given by the thickness of the thickest part of the intermediate layer 33. However, the value of $T3_{min}/T3_{max}$ is preferably in the range of 0.05 to 0.95, and more preferably in the range of 0.1 to 0.6.

According to the flexible tube 1C having the structure described above, in spite of the fact that the total thickness of the outer cover 3 (excluding the portions of the projections 4) is substantially uniform over its entire region, the ratio of the thickness of the intermediate layer 33 to that of each of the inner and outer layer 31 and 32 becomes larger at a portion closer to the tip end 12. This structure makes it possible for the flexible tube 1C to have higher stiffness against tension and bending at a portion closer to the "base" end 11, and to have higher flexibility at a portion closer to the "tip" end 12. In other words, this structure makes it possible for the flexible tube 1C to have flexibility which gradually varies in the longitudinal direction.

According to the flexible tube for an endoscope as described above, since the flexible tube has higher stiffness in a portion closer to the base end 11, it is possible to fully transmit to the tip end 12 the push-in force and the rotational force applied by the operator. On the other hand, the flexible tube has higher flexibility in a portion closer to the tip end 12, it is also possible to smoothly insert an insertion section (flexible tube) of an endoscope into an internal curved portion of a patient in a safe manner. Therefore, the flexible tube as described above makes it possible for an operator to insert the insertion section with easy manipulation, thus enabling the reduction of the burden on the patient during the endoscopic examination.

Further, according the flexible tube 1C of this embodiment, the outer cover 3 is formed such that the thickness of one of the inner and intermediate layers 31 and 33 decreases in the opposite direction to the other layer. This results in that the flexible tube 1C has a uniform outer diameter over its entire region. When such a flexible tube having a uniform outer diameter is actually used, it is possible to reduce the burden on the patient during endoscopic examination.

V. Fourth Embodiment (Flexible Tube 1D)

Figure 5:
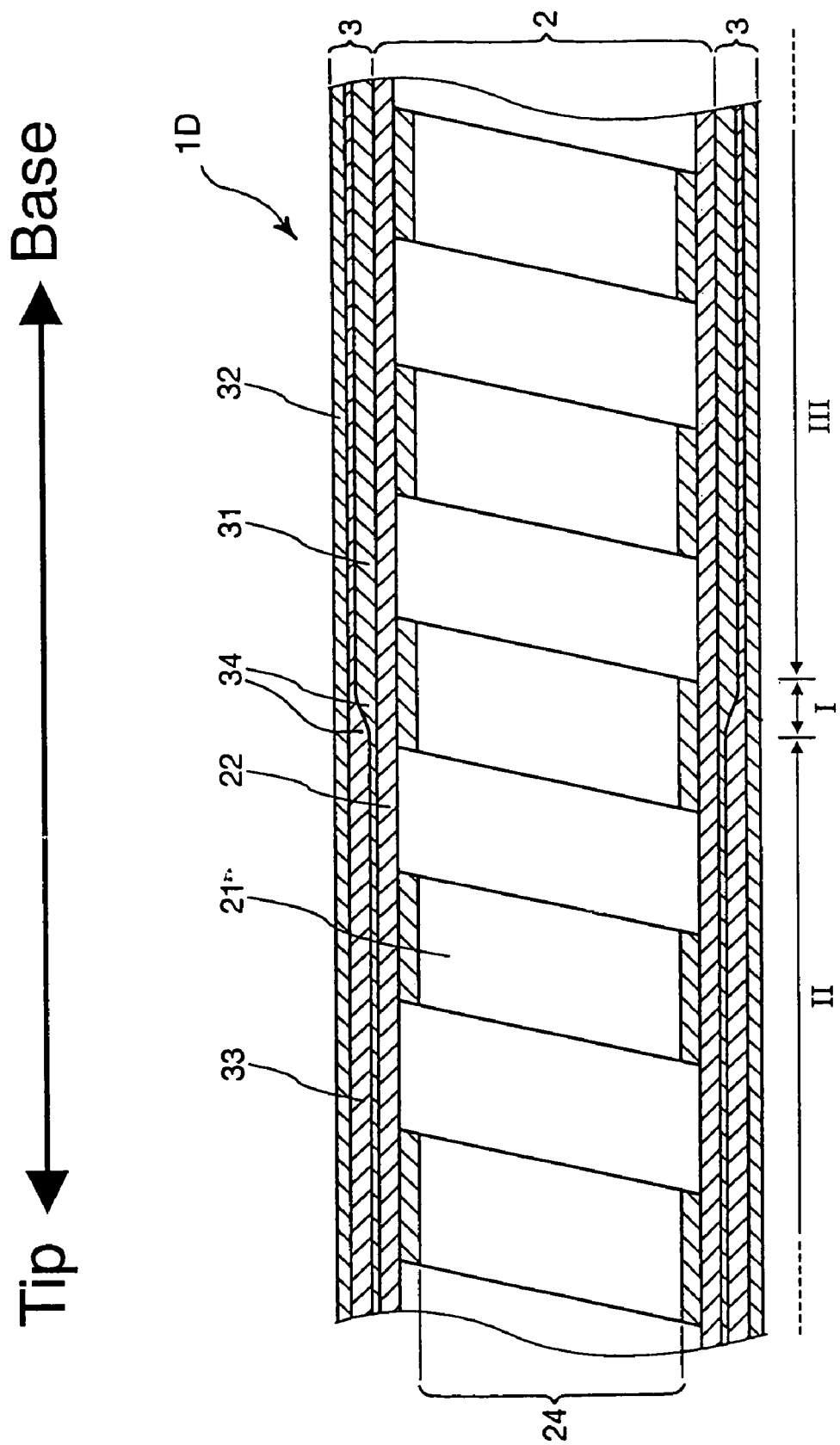
FIG. 5 is a sectional view which shows a part of a fourth embodiment of the flexible tube according to the present invention.

Next, a fourth embodiment of the flexible tube for an endoscope will be described with reference to FIG. 5. FIG. 5 is a sectional view which shows a part of a flexible tube 1D according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1. (i.e., side closer to an operator), and the left-hand side corresponds, to the side of tip end 12 shown in FIG. 1. Further, in this figure, the reference numeral "I" indicates a region where a thickness-varying region is formed, and each of the reference numerals "II" and "III" indicates a region where no thickness-varying region is formed. (In this description, a region within which the thickness of a layer increases or decreases is referred to as a "thickness-varying region" of the layer.) In this connection, it is to be noted that the total length of the regions I, II and III corresponds to the length of an outer cover 3 of the flexible tube 1D.

As shown in FIG. 5, the outer cover 3 of the flexible tube 1D has a laminate structure composed of inner, outer and intermediate layers 31–33. Each of the inner and intermediate layers 31 and 33 has a thickness-varying region 34 within the region I, and the outer layer 32 has a substantially uniform thickness over its entire region. The thickness-varying region of each of the inner and intermediate layers 31 and 33 has a relatively small length (e.g., approximately 5 to 80 mm). In this embodiment, the intermediate layer 33 is formed of a material having higher elasticity than that of the inner layer 31.

The thickness-varying region 34 of the inner layer 31 is formed at a specific portion of this layer (i.e., within the region I), and as shown in FIG. 5 the thickness of this thickness-varying region 34 gradually decreases within the region I in the direction from the base end 11 toward the tip end 12. Within the regions II and III the inner layer 31 has a substantially uniform thickness, but it has larger thickness within the region III as compared with the thickness within the region II.

Similarly the thickness-varying region 34 of the intermediate layer 33 is also formed within the region I, and as shown in FIG. 5 the thickness of this thickness-varying region 34 gradually decreases within the region I in the direction from the tip end 12 toward the base end 11 (i.e., in the direction opposite to that of the thickness-varying region 34 of the inner layer 31). Within the regions II and III the intermediate layer 32 has a substantially uniform thickness, but it has larger thickness within the region II as compared with the thickness within the region III.

It is to be noted that in this embodiment the outer cover 3 having the inner, outer and intermediate layers 31–33 is formed so that the thickness-varying regions 34 of the inner and intermediate layers 31 and 33 face (overlap) each other in the thickness direction as shown in FIG. 5. Further, it is also to be noted that the total thickness of the inner and intermediate layers 31 and 33 remains substantially uniform over the entire region of the flexible tube 1D in spite of the fact that these layers have a thickness-varying region.

According to the flexible tube 1D having the structure described above, since the intermediate layer 33 is formed of a material having higher elasticity than that of the inner layer 31, the outer cover 3 has a relatively high stiffness (low flexibility) within the region III, while it has a relatively low stiffness (high flexibility) within the region II. In addition, the outer cover 3 has a medium stiffness within the region I where the thickness-varying regions 34 are formed, and the stiffness of this portion varies in the longitudinal direction. The structure described above gives higher stiffness to the base side region (region III) of the flexible tube 1D, while it gives higher flexibility to the tip side region (region II) of the flexible tube 1D. In addition, the structure described above makes it possible to form a flexible tube such that its stiffness (flexibility) varies gradually or stepwise within a portion where a thickness-varying region(s) is formed. According to such a flexible tube, since it has higher stiffness in a portion closer to the base end 11, it is possible to fully transmit to the tip end 12 the push-in force and the rotational force applied by the operator. On the other hand, the flexible tube has high flexibility in a portion closer to the tip end 12, it is also possible to smoothly insert an insertion section (flexible tube) of an endoscope into an internal curved portion of a patient in a safe manner. Therefore, the flexible tube as described above makes it possible for an operator to insert the insertion section with easy manipulation, thus enabling the reduction of the burden on the patient during the endoscopic examination.

Further, according the flexible tube 1D in this embodiment, the flexible tube 1D has a uniform outer diameter over its entire region in spite of the fact that each of the inner and intermediate layers 31 and 33 has a thickness-varying region 34. Therefore, when such a flexible tube having a uniform outer diameter is used, it is possible to reduce the burden on the patient during endoscopic examination.

VI. Fifth Embodiment (Flexible Tube 1E)

Figure 6:
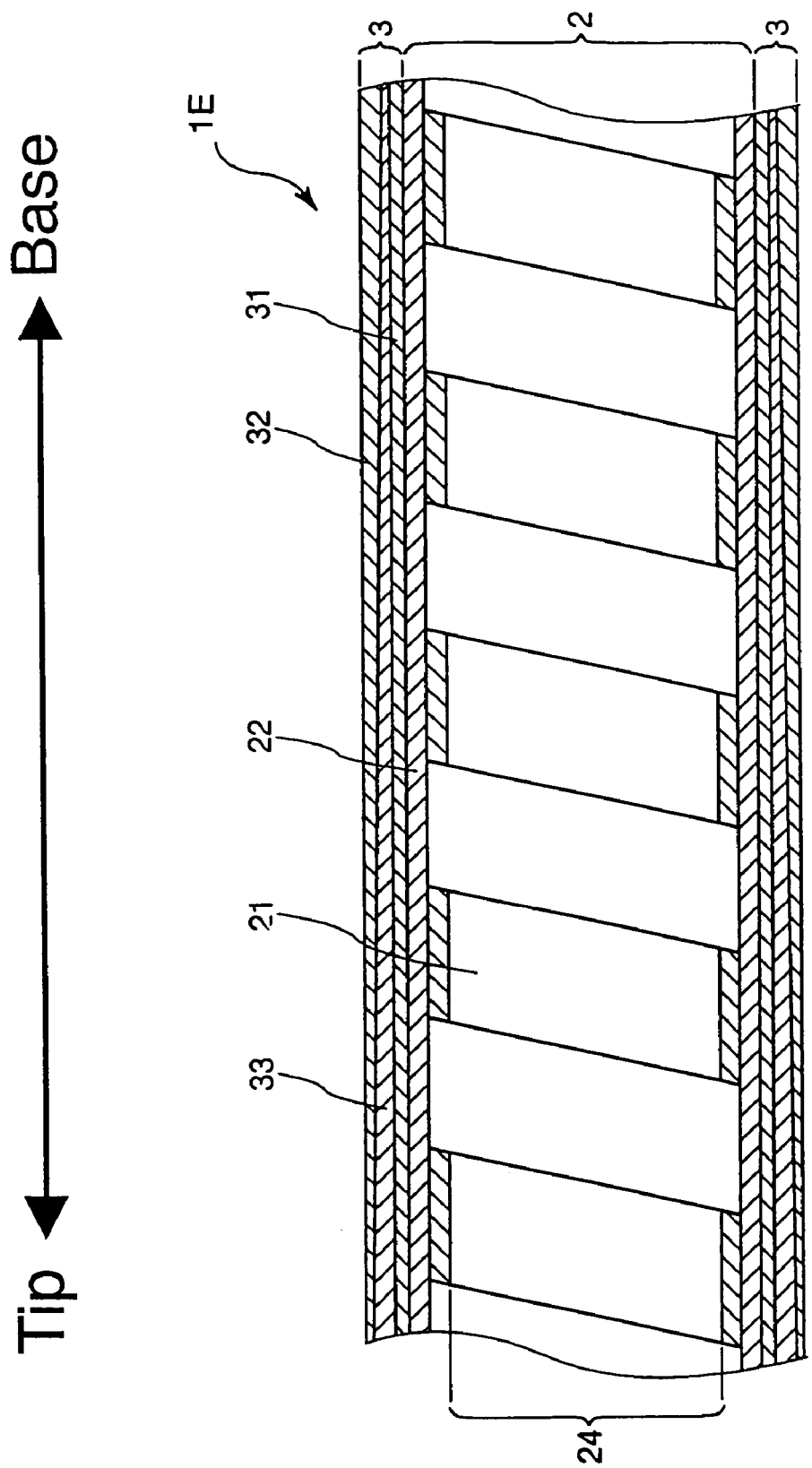
FIG. 6 is a sectional view which shows a part of a fifth embodiment of the flexible tube according to the present invention.

Next, a fifth embodiment of the flexible tube for an endoscope will be described with reference to FIG. 6. FIG. 6 is a sectional view which shows a part of a flexible tube 1E according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1.

In this embodiment, an outer cover 3 of the flexible tube 1E has a laminate structure composed of inner, outer and intermediate layers 31–33. The inner layer 31 has a substantially uniform thickness over its entire region. The thickness of each of the outer and intermediate layers 32 and 33 varies over the entire region. As shown in FIG. 6, the thickness of the outer layer 32 gradually "decreases" in the direction from the base end 11 toward the tip end 12. Conversely, the thickness of the intermediate layer 33 gradually "increases" in the direction from the base end 11 toward the tip end 12. In this embodiment, the intermediate layer 33 is formed of a material having higher elasticity than that of the outer inner layer 31.

In this connection, it is to be noted that the thickness of the intermediate layer 33 decreases in the opposite direction to that of the outer layer 32. Further, it is also to be noted that the total thickness of the outer and intermediate layers 32 and 33 remains substantially uniform over the entire region of the flexible tube 1E, and the thickness of the outer cover 3 remains substantially uniform over its entire region in spite of the fact that the thickness of each of the outer and intermediate layers 32 and 33 varies over its entire region.

In this embodiment, the value of $T2_{min}/T2_{max}$ is not particularly limited, where the value of "$T2_{min}$" is given by the thickness of the thinnest part of the outer layer 32, and the value of "$T2_{max}$" is given by the thickness of the thickest part of the outer layer 32. However, the value of $T2_{min}/T2_{max}$ is preferably in the range of 0.05 to 0.95, and more preferably in the range of 0.1 to 0.6.

According to the flexible tube 1E of this invention, it is possible to achieve the same advantages as those described with respect to the flexible tube 1C (FIG. 4) in the third embodiment.

VII. Sixth Embodiment (Flexible Tube 1F)

Figure 7:
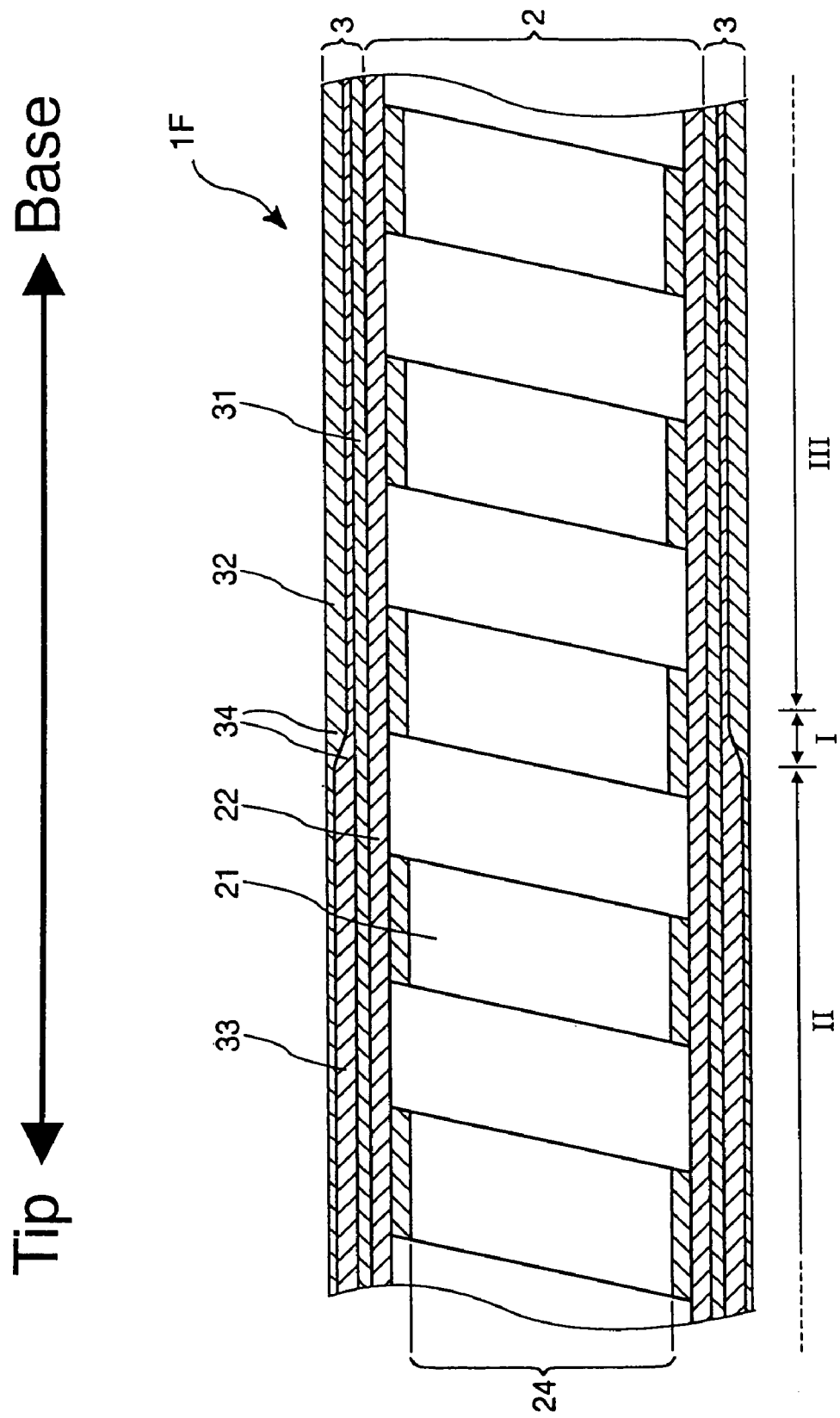
FIG. 7 is a sectional view which shows a part of a sixth embodiment of the flexible tube according to the present invention.

Next, a sixth embodiment of the flexible tube for an endoscope will be described with reference to FIG. 7. FIG. 7 is a sectional view which shows a part of a flexible tube 1F according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1. Further, in this figure, the reference numeral "I" indicates a region where a thickness-varying region is formed, and each of the reference numerals "II" and "III" indicates a region where no thickness-varying region is formed. In this connection, it is to be noted that the total length of the regions I, II and III corresponds to the length of an outer cover 3 of the flexible tube 1F.

As shown in FIG. 7, the outer cover 3 of the flexible tube 1F has a laminate structure composed of inner, outer and intermediate layers 31–33. Each of the outer and intermediate layer 32 and 33 has a thickness-varying region 34 within the region I, and the inner layer 31 has a substantially uniform thickness over its entire region. The thickness-varying region 34 of each of the outer and intermediate layers 32 and 33 has relatively small length (e.g., approximately 5 to 80 mm). In this embodiment, the intermediate layer 33 is formed of a material having higher elasticity than that of the outer layer 32.

The thickness-varying region 34 of the outer layer 32 is formed at a specific portion of this layer (i.e., within the region I), and as shown in FIG. 7 the thickness of this thickness-varying region 34 gradually decreases within the region I in the direction from the base end 11 toward the tip end 12. Within the regions II and III the outer layer 32 has a substantially uniform thickness, but it has larger thickness within the region III as compared with the thickness within the region II.

Similarly the thickness-varying region 34 of the intermediate layer 33 is also formed within the region I, but as shown in FIG. 7 the thickness of this thickness-varying region 34 gradually decreases within the region I in the direction from the tip end 12 toward the tip end 12 (i.e., in the direction opposite to that of the thickness-varying region 34 of the outer layer 32). Within the regions II and III the intermediate layer 33 has a substantially uniform thickness, but it has larger thickness within the region II as compared with the thickness within the region III.

It is to be noted that in this embodiment the outer cover 3 having the inner, outer and intermediate layers 31–33 is formed so that the thickness-varying regions 34 of the outer and intermediate layers 32 and 33 face (overlap) each other in the thickness direction as shown in FIG. 7. Further, it is also to be noted that the total thickness of the outer and intermediate layers 32 and 33 remains substantially uniform over the entire region of the outer cover 3 in spite of the fact that each of the outer and intermediate layers 32 and 33 has a thickness-varying region.

According to the flexible tube 1F of this invention, it is possible to achieve the same advantages as those described with respect to the flexible tube 1D in the fourth embodiment.

VIII. Examples of Second–Sixth Embodiments

Next, specific examples of the second–sixth embodiments described above will be described below.

1. Preparation of Flexible Tube for an Endoscope

Example 2a

First, a coil 21 having an outer diameter of 9.9 mm and an inner diameter of 9.6 mm was prepared by winding a band-shaped stainless steel material having a width of 3 mm. Next, stainless steel fine wires 23 at least one of which had been given a coating of a polyamide resin and each of which had a diameter of 0.1 mm were prepared, and then using these fine wires a plurality of bundles of ten fine wires were prepared. These bundles of the ten fine wires 23 were woven together in a lattice manner to obtain a reticular tube 22. Then, the obtained reticular tube 22 was provided on the prepared coil 21 so that the outer periphery of the coil 21 was covered with the reticular tube 22. In this way, a core body 2 was prepared.

Next, using an extrusion-molding machine, an outer cover 3 composed of inner, outer and intermediate layers 31–33 was provided on the outer periphery of the core body 2 so that the core body 2 was covered with the outer cover 3. (A constituent material used for each of the layers in this Example is as shown in the attached Table 2.) In this way, a flexible tube for an endoscope with a length of 1.6 m was prepared. In this connection, it is to be noted that the length of 1.6 m means the length of an available (effective) portion of the flexible tube that can be used for a flexible tube for an endoscope, that is the length of 1.6 m means an available (effective) length of the flexible tube. Therefore, the actually prepared flexible tube had a length more than 1.6 m by including additional portions at the both ends of the available portion of the flexible tube (See FIG. 13). In this regard, however, it goes without saying that the available length is not limited to 1.6 m mentioned above.

In the preparation described above, the outer cover 3 was provided over the core body 2 such that the thickness of the inner layer 31 gradually increases at a constant rate between both ends 11 and 12 of the flexible tube in the direction from the tip end 12 toward base end 11. Specifically, the inner layer 31 was formed over the entire region (length) of the outer cover 3 so as to have a thickness of 0.05 mm ($T1_{min}$) at the tip end 12 and have a thickness of 0.44 mm ($T1_{max}$) at the base end 11. In the inner layer 31 of the prepared flexible tube, the $T1_{min}/T1_{max}$ had a value of 0.125, where the value of "$T1_{min}$" is given by the thickness of the thinnest part of the inner layer 31, and the value of "$T1_{max}$" is given by the thickness of the thickest part of the inner layer 31.

In addition, the intermediate layer 33 was formed such that its thickness gradually decreases at a constant rate between the both ends 11 and 12 in the direction from the tip end 12 toward base end 11. Specifically, the intermediate layer 33 was formed over the entire region (length) of the outer cover 3 so as to have a thickness of 0.05 mm ($T3_{min}$) at the base end 11 and have a thickness of 0.4 mm ($T3_{max}$) at the tip end 12. In the intermediate layer 33 of the prepared flexible tube, the $T3_{min}/T3_{max}$ had a value of 0.125, where the value of "$T3_{min}$" is given by the thickness of the thinnest part of the intermediate layer 33, and the value of "$T3_{max}$" is given by the thickness of the thickest part of the intermediate layer 33.

The outer layer 32 of the outer cover 3 was formed over the entire region (length) of the outer cover 3 so as to have a uniform thickness (0.1 mm).

Example 2b

A flexible tube for an endoscope was prepared in the same manner as in Example 2a except that the thickness (shape) of each layer of an outer cover 3 was changed as follows.

In the preparation of the flexible tube, the outer cover 3 was provided over the core body 2 such that the thickness of the outer layer 32 gradually increases at a constant rate between both ends 11 and 12 of the flexible tube in the direction from the tip end 12 toward base end 11. Specifically, the outer layer 32 was formed over the entire region (length) of the outer cover 3 so as to have a thickness of 0.05 mm ($T2_{min}$) at the tip end 12 and have a thickness of 0.4 mm ($T2_{max}$) at the base end 11. In the inner layer 31 of the prepared flexible tube, the $T2_{min}/T2_{max}$ had a value of 0.125, where the value of "$T2_{min}$" is given by the thickness of the thinnest part of the outer layer 32, and the value of "$T2_{max}$" is given by the thickness of the thickest part of the outer layer 32.

In addition, the intermediate layer 33 was formed such that its thickness gradually decreases at a constant rate between the both ends 11 and 12 in the direction from the tip end 12 toward base end 11. Specifically, the intermediate layer 33 was formed over the entire region (length) of the outer cover 3 so as to have a thickness of 0.05 mm ($T3_{min}$) at the base end 11 and have a thickness of 0.4 mm ($T3_{max}$) at the tip end 12. In the intermediate layer 33 of the prepared flexible tube, the $T3_{min}/T3_{max}$ had a value of 0.125, where the value of "$T3_{min}$" is given by the thickness of the thinnest part of the intermediate layer 33, and the value of "$T3_{max}$" is given by the thickness of the thickest part of the intermediate layer 33.

The inner layer 31 of the outer cover 3 was formed over the entire region (length) of the outer cover 3 so as to have a uniform thickness (0.1 mm).

Example 2c

A flexible tube for an endoscope was prepared in the same manner as in Example 2a except that the thickness (shape) of each layer of an outer cover 3 was changed as follows.

In the preparation of the flexible tube, the outer layer 32 of the outer cover 3 was formed such that its thickness increases stepwise in four steps in the direction from the tip end 12 to the base end 11. Specifically, the outer layer 32 was formed over the entire region (length) of the outer cover 3 so as to have a thickness of 0.05 mm at a first quarter (that is closest to the tip end 12) of the entire region; have a thickness of 0.15 mm at a second quarter adjacent to the first quarter; have a thickness of 0.25 mm at a third quarter adjacent to the second quarter; and have a thickness of 0.4 mm at a fourth quarter (that is closest to the base end 11) adjacent to the third quarter. In this outer layer 32, the tip end 12 had a thickness of 0.05 mm ($T2_{min}$), and the base end 11 had a thickness of 0.4 mm ($T2_{max}$). Thus, the $T2_{min}/T2_{max}$ had a value of 0.125, where the value of "$T2_{min}$" was given by the thickness of the thinnest part of the outer layer 32, and the value of "$T2_{max}$" was given by the thickness of the thickest part of the outer layer 32.

Further, the intermediate layer 33 of the outer cover 3 was formed such that the thickness decreases stepwise in four steps in the direction from the tip end 12 to the base end 11. Specifically, the intermediate layer 33 had been formed over the entire region (length) of the outer cover 3 so as to have a thickness of 0.4 mm at a first quarter (that is closest to the tip end 12) of the entire region; have a thickness of 0.25 mm at a second quarter adjacent to the first quarter; have a thickness of 0.15 mm at a third quarter adjacent to the second quarter; and have a thickness of 0.05 mm at a fourth quarter (that is closest to the base end 11) adjacent to the third quarter. In this intermediate layer 33, the tip end 12 had a thickness of 0.05 mm ($T3_{min}$), and the base end 11 had a thickness of 0.44 mm ($T3_{max}$). Thus, the $T3_{min}/T3_{max}$ had a value of 0.125, where the value of "$T3_{min}$" was given by the thickness of the thinnest part of the intermediate layer 33, and the value of "$T3_{max}$" was given by the thickness of the thickest part of the intermediate layer 33.

In addition, the inner layer 31 of the outer cover 3 was formed over the entire region (length) of the outer cover 3 so as to have a uniform thickness (0.1 mm).

Example 2d

A flexible tube for an endoscope was prepared in the same manner as in Example 2b except that the thickness (shape) of an outer layer 32 of an outer cover 3 was changed as follows, and a constituent material for the outer layer 32 was changed as shown in the attached Table 2.

In the preparation of the flexible tube, the outer cover 3 was provided over the core body 2 such that the thickness of the outer layer 32 gradually increases at a constant rate between the both ends 11 and 12 of the flexible tube in the direction from the tip end 12 toward base end 11. Specifically, the outer layer 32 was formed over the entire region (length) of the outer cover 3 so as to have a thickness of 0.1 mm ($T2_{min}$) at the tip end 12 and have a thickness of 0.45 mm ($T2_{max}$) at the base end 11. In the outer layer 32 of the prepared flexible tube, the $T2_{min}/T2_{max}$ had a value of 0.222, where the value of "$T2_{min}$" was given by the thickness of the thinnest part of the outer layer 32, and the value of "$T2_{max}$" was given by the thickness of the thickest part of the outer layer 32.

Example 2e

A flexible tube for an endoscope was prepared in the same manner as in Example 2a except that a material for an outer layer 32 of an outer cover 3 was changed as shown in the attached Table 2.

Comparative Example 2a

A core body 2 was prepared in the same manner as in Example 2a. Then, using an extrusion-molding machine, an outer cover 3 composed of two layers (i.e., inner and outer layers 31 and 32) was provided on the outer periphery of the core body 2 so that the core body 2 was covered with the outer cover 3. In this way, a flexible tube for an endoscope with a length of 1.6 m was prepared. A constituent material for each layer of the outer cover 3 is shown in the attached Table 2.

In the preparation of the flexible tube in this embodiment, the inner layer 31 of the outer cover 3 was formed over the entire region (length) of the outer cover 3 so as to have a uniform thickness (0.2 mm). Further, the outer layer 32 of the outer cover 3 was formed over the entire region (length) of the outer cover 3 so as to have a uniform thickness (0.3 mm).

Comparative Example 2b

A flexible tube for an endoscope was prepared in the same manner as in Comparative Example 2a except that a material for an outer layer 32 was changed as shown in the attached Table 2.

Comparative Example 2c

A flexible tube for an endoscope was prepared in the same manner as in Comparative Example 2a except that a material for each of inner and outer layers 31 and 32 was changed as shown in the attached Table 2.

2. Observation of the Prepared Flexible Tubes

An observation of the cross-section of the outer cover 3 was carried out for each of the flexible tubes of Examples 2a–2e and Comparative Examples 2a–2c. Through the observation, formation of projections 4 as shown in FIG. 2 was observed in each of the flexible tubes of Examples 2a–2e and Comparative Examples 2a and 2b, but no formation of projections 4 was observed in the flexible tube of Comparative Example 2c.

3. Measurement of Rate of Change in Bending Stiffness

The rate of change in the bending stiffness in the longitudinal direction was measured for each of the flexible tubes of Examples 2a–2e.

Figure 13:
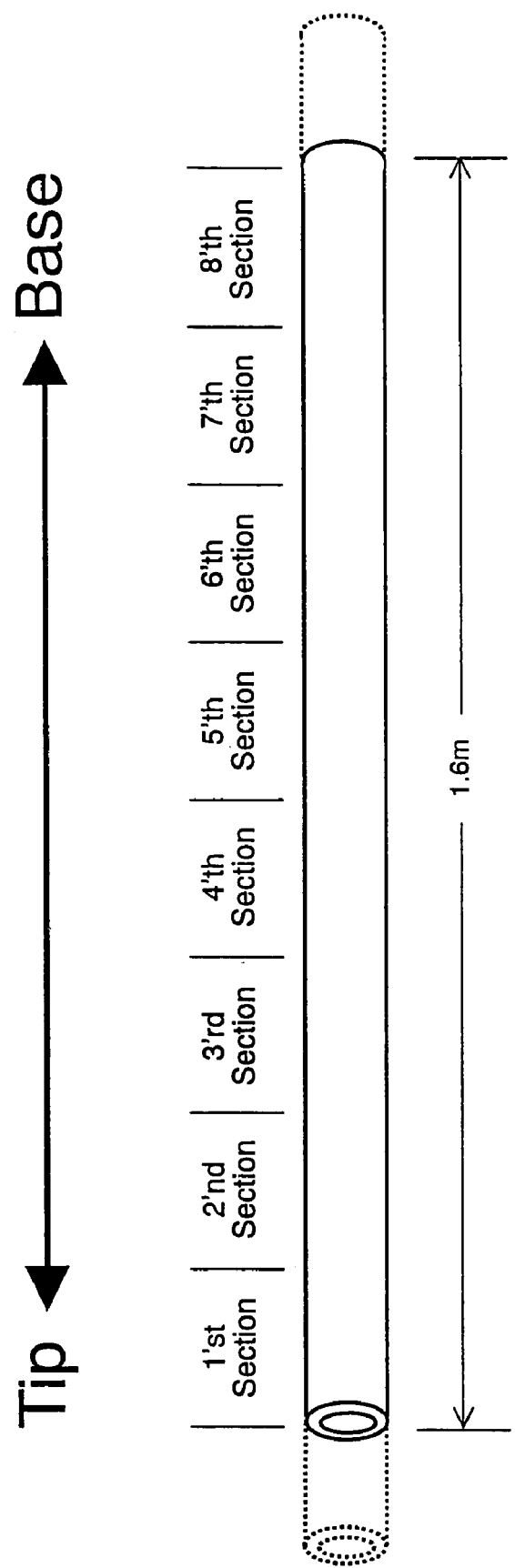
FIG. 13 is an illustration which shows a state where an flexible tube is divided into eight sections.

For each flexible tube, first the flexible tube was divided into eight sections (i.e., first–eighth sections as shown in FIG. 13) which have an equal length (200 mm) in the longitudinal direction, and then the bending stiffness in "each" of the eight sections of the flexible tube was measured according to the following method.

Figure 15:
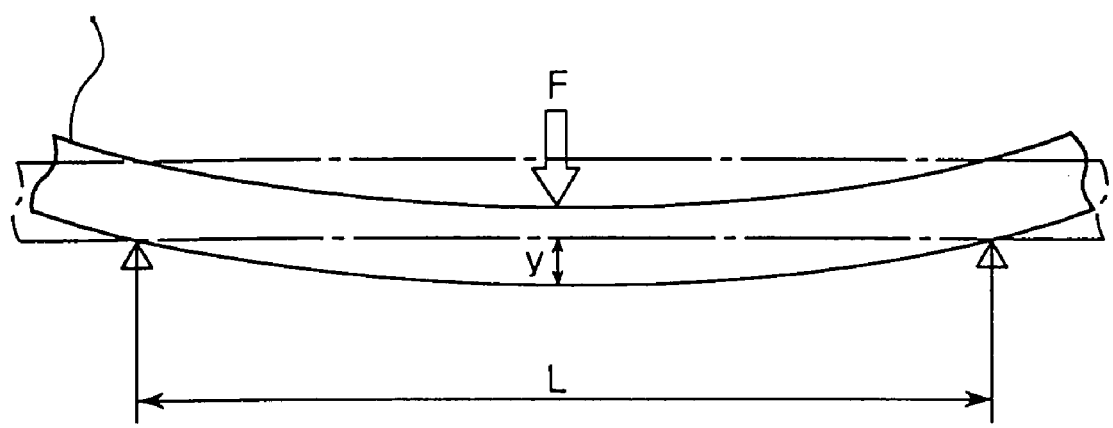
FIG. 15 is an illustration which shows a state where the bending stiffness in one of the sections shown in FIG. 13 or 14 is measured.

In the measurement, as shown in FIG. 15, first the flexible tube was laid on two supporting-points located a distance L (200 mm) a part so that both ends of one of the sections were supported by the two supporting-points. Then, the magnitude of the pressing force F when the central point of the section was displaced downward by a predetermined distance y (50 mm) was measured and defined as the bending stiffness of each section. Based on the measured value, the rate of change in the bending stiffness in the longitudinal direction of the flexible tube was calculated. The results of the measurement are shown in the attached Table 3.

4. Evaluation of Flexible Tube (4-1) Insertion (Operationability) Test

An insertion test was carried out for each of the flexible tubes of Examples 2a–2e and Comparative Examples 2a–2c to evaluate operationability (i.e., degree of easiness in insertion operation) of an endoscope with the flexible tube.

Before carrying out the insertion test, endoscopes as shown in FIG. 1 were prepared using the flexible tubes of Examples 2a–2e and Comparative Examples 2a–2c. Further, a living body model having an internal structure similar to an internal portion of a human body was prepared. Then, each of the prepared endoscopes was inserted into the internal portion of the living body model until its tip end (i.e., tip of an bendable tube 5) reaches a portion corresponding to a large intestine of a human body. In the insertion test, the operationability of the endoscope during the insertion operation was evaluated in accordance with the four rankings A–D given below.

Rank A:
It is possible to perform insertion operation very smoothly. (A flexible tube of an endoscope of Rank A is considered to be best suited for use as a flexible tube for an endoscope.)

Rank B:
It is possible to perform insertion operation smoothly. (A flexible tube of an endoscope of Rank B is considered to be suited for use as a flexible tube for an endoscope.)

Rank C:
It takes a relatively long time to complete insertion operation. (A flexible tube of an endoscope of Rank C is considered to have problems for use as a flexible tube for an endoscope.)

Rank D:
It is difficult to complete insertion operation. (A flexible tube of an endoscope of Rank D is considered to be unsuited for use as a flexible tube for an endoscope.)

The results of the insertion test are shown in the attached Table 4.

(4-2) Chemical Resistance Test

A chemical resistance test was carried out for each of the flexible tubes of Example 2a–2e and Comparative Example 2a–2c. In the chemical resistance test, 100L of 10% aqueous solution of iodine held at 25° C. was prepared first, and then each of the prepared flexible tubes was immersed in the aqueous solution for 200 hours. Then, the condition of each flexible tube was evaluated in accordance with the four rankings A–D given below.

Rank A:
No Change in the Appearance; and
No Occurrence of Cracks and Blisters in Outer Cover.

Rank B:
Slight Change in the Appearance; and
Occurrence of Blisters at a Few Spots of Outer Cover.

Rank C:
Large Change in the Appearance; and
Occurrence of Blisters at Many Spots of Outer Cover.

Rank D:
Extremely Large Change in the Appearance; and
Occurrence of a Large Number of Cracks and Blisters on Outer Cover.

The evaluation result in this test is shown in the attached Table 4.

(4-3) Durability Test

A durability test was carried out to examine durability of each of the flexible tubes of Example 2a–2e and Comparative Example 2a–2c. In the durability test, each of the flexible tubes was set to a state where the flexible tube was supported at its both ends, and in this state the operation of bending by 90° was repeated 300 times for each flexible tube. Then, the degree of change in the flexibility after the repeated operation of bending was examined to evaluate the durability of the flexible tube in accordance with the four rankings A–D given below.

Rank A:
Almost No Change in Flexibility
(A flexible tube of Rank A is considered to have extremely high durability.)

Rank B:
Slight Lowering of Flexibility
(A flexible tube of Rank B is considered to have high durability.)

Rank C:
Large Lowering of Flexibility
(A flexible tube of Rank C is considered to have problems in the durability.)

Rank D:
Extremely Large Lowering of Flexibility; and
Occurrence of cracks and the like at many spots of the outer cover.
(A flexible tube of Rank D is considered to be unsuited for use as a flexible tube for an endoscope.)

The result of the durability test is shown in the attached Table 4.

(4-4) Evaluation

The results in the attached Tables 3 and 4 show that the flexible tube according to the present invention (i.e., Examples 2a–2e) has excellent operationability and high chemical resistance as well as high durability. Further, the results in the attached Table 4 also show that conventional flexible tubes (i.e., Comparative Examples 2a–2c) have some drawbacks.

Specifically, the flexible tube of Comparative Example 2a has poor resistance to chemical. This drawback is considered to result from the fact that the outer layer 32 of the outer cover 3 was formed of the material having poor chemical resistance. Further, the flexible tube of Comparative Example 2b has poor operationability. Furthermore, the flexible tube of Comparative Example 2c has poor durability as well as poor operationability. The poor durability of this flexible tube is considered to result from the fact that no projections 4 as shown in FIG. 2 were formed on the inner layer 31.

According to the present invention described above, appropriate materials that are for each of layers of an outer cover 3 are used for preparing the outer cover, and the outer cover 3 is provided onto the core body so that each of the layers has appropriate thickness and shape. This structure and the selection of material make it possible to produce a flexible tube for an endoscope that has high durability, high flexibility, and high chemical resistance as well as excellent operationability.

Further, according to the present invention, the outer cover of the flexible tube is formed so that the thickness of at least one of layers constituting the outer cover (laminate structure) varies in the longitudinal direction, for example, gradually or stepwise. This configuration makes it possible for an operator to insert an insertion section (flexible tube) of an endoscope into a body cavity of a living body with easy manipulation.

Furthermore, according to the present invention, a material having high elasticity is used for an intermediate layer of the outer cover. This makes it possible to give high flexibility to a flexible tube, thus enabling the operator to insert an insertion section of an endoscope more easily.

Moreover, according to the present invention, a material having high resistance to chemical is used for an outer layer of the outer cover. This makes it possible to give high chemical resistance to a flexible tube.

In addition, according to the present invention, a material having high adhesion with a core body 2 is used for an inner layer of an outer cover. This makes it possible to give high durability to a flexible tube.

IX. Seventh Embodiment (Flexible Tube 1G)

Figure 8:
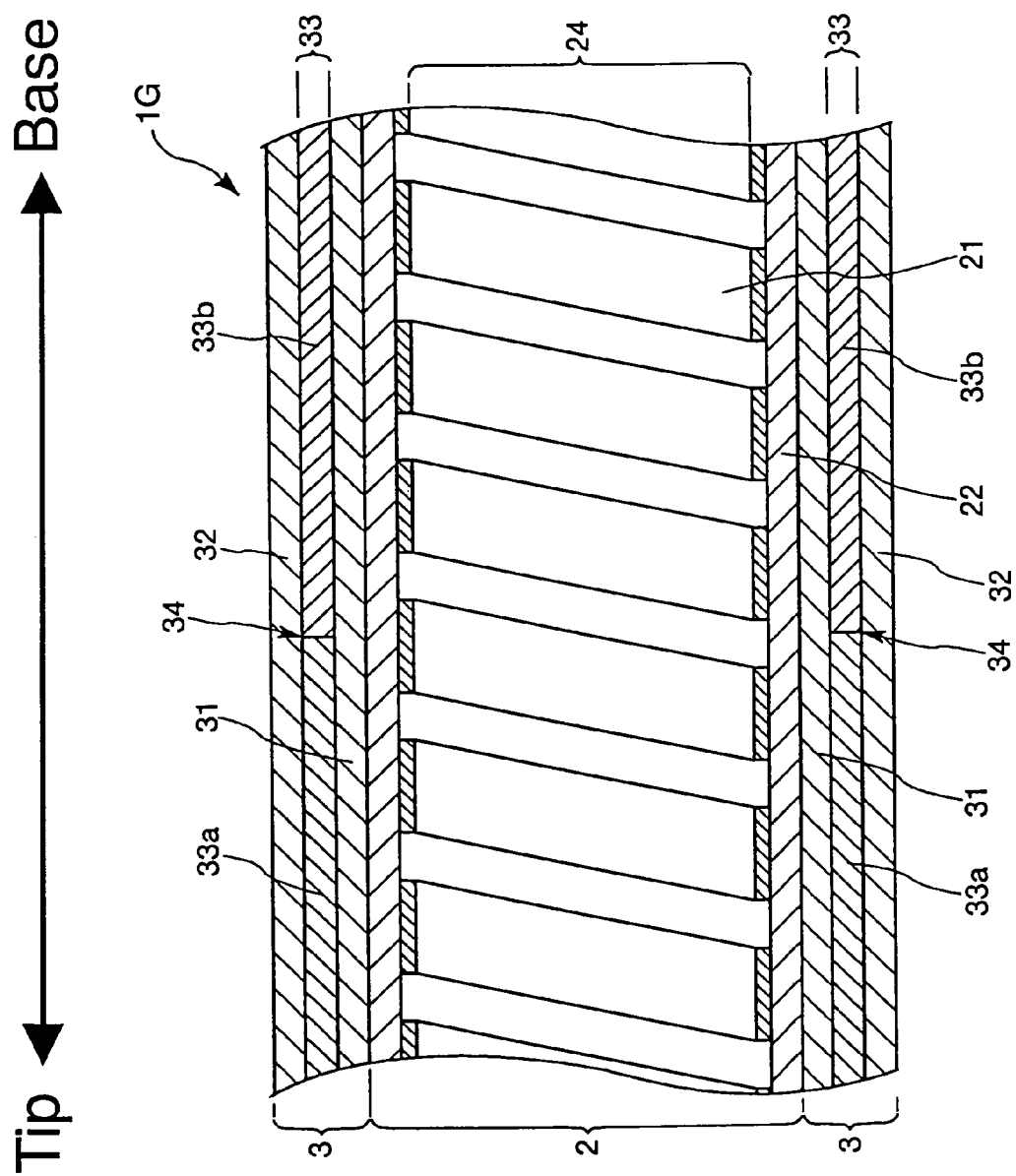
FIG. 8 is a sectional view which shows a part of a seventh embodiment of the flexible tube according to the present invention.

Next, a seventh embodiment of the flexible tube for an endoscope will be described with reference to FIG. 8. FIG. 8 is a sectional view which shows a part of a flexible tube 1G according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1.

An outer cover 3 of the flexible tube 1G has a laminate structure composed of inner, outer and intermediate layers 31–33. The inner and outer layers 31 and 32 have the same structures as those of the flexible tube 1A in the first embodiment, and this embodiment is different from the first embodiment in the structure of the intermediate layer 33. The structure of the intermediate layer 33 is described below in detail.

The intermediate layer 33 is formed between the inner layer 31 and the outer layer 32. As shown in FIG. 8, this intermediate layer 33 has a first portion (first region) 31a formed at a position closer to the tip end 12, and a second portion (second region) 33b formed at a position closer to the base end 11. The first and second portions 33a and 33b are contiguous to each other through a boundary 34. Specifically, the first portion 33a is formed within a region from the tip end 12 to the boundary 34, and the second portion 33b is formed within a region from the boundary section 34 to the base end 11.

The first portion 33a is different from the second portion 33b and 33b in its physical property or chemical property. (Hereinafter, the physical property and chemical property will be referred to simply as "property.") However, the property within each of the first and second portions 33a and 33b is substantially homogeneous. As a result of this structure, the property of the intermediate layer 33 varies substantially stepwise at the boundary 34. Such a difference in the property between the first and second portions 33a and 33b can be obtained by constituting the first and second portions 33a and 33b with different materials.

The lengths of the first and second portions 33a and 33b in the longitudinal direction may differ depending on the type of an endoscope or the like. However, in this invention, it is preferable that the length of the first portion 33a is in the range of about 50 to 1000 mm, and more preferably about 100 to 700 mm. Further, it is preferable that the length of the second portion 33b is in the range of about 50 to 1000 mm, and more preferably 100 to 700 mm.

In addition, in this invention, it is preferable that the first portion 33a is formed of a material having a lower hardness (stiffness) than that of the second portion 33b. With this arrangement, the tip side portion of the outer cover 3 where the first portion 33a is formed has a lower stiffness against tension, bending and the like than that of the base side portion of the outer cover 3 where the second portion 33b is formed. Therefore, by forming the outer cover 3 so as to have two distinct portions (i.e., first and second portion 33a and 33b), it becomes possible to give the tip side region of a flexible tube a higher flexibility than that of the base side region.

According to the flexible tube 1G having the intermediate layer 33 as described, the flexible tube 1G has a high "stiffness" in the portion near the base end 11 (where the second portion 33b is formed) so that a push-in force and the rotational force applied by the operator are sufficiently transmitted to the tip end 12, while it has a high "flexibility" in the portion near the tip end 12 (where the first portion 33a is formed) so that the tip side region of the flexible tube is smoothly inserted into and follows the body cavity having curved form. This structure makes it possible to improve the operationability of the endoscope when inserting the insertion section (flexible tube) into an internal portion of the living body. Accordingly, when an endoscope with the flexible tube having the structure as described above is used during an endoscopic examination, it is possible to reduce burden on a patient, since the operator can safely and smoothly perform the insertion operation.

In this invention, it is preferable the intermediate layer 33 has a higher elasticity than that of the outer layer 32, and more preferably the intermediate layer 33 has a higher elasticity than that of any one of the inner and outer layers 31 and 32. With this arrangement, the intermediate layer 33 functions as a cushioning layer (cushioning means) between the inner layer 31 and the outer layer 32. (In the following, such a function given by the intermediate layer 33 is referred to as "cushioning function.") Accordingly, by forming the, intermediate layer 33 as described above, it is possible to give higher flexibility to the flexible tube.

Hereinafter, the cushioning function of the intermediate layer 33 is described in more detail. When the flexible tube 1G is bent by an external force, the high elastic force is generated in the bent intermediate layer 33 through the deformation thereof The generated elastic force is transmitted effectively to the inner layer 31 and the outer layer 32, respectively, since the intermediate layer 33 is sandwiched between the inner layer 31 and the outer layer 32 each of which has relatively low elasticity. When the external force has been removed, the bent flexible tube 1G is restored to its original shape by the high elastic force generated in the bent intermediate layer 33. In this connection, it is to be noted that the restoration of the flexible tube into its original shape is achieved by the cushioning function of the intermediate layer 33, and that such a cushioning function gives the flexible tube high flexibility.

In this embodiment, a constituent material for the intermediate layer 33 is not particularly limited. Examples of such material include various resins having elasticity such as polyvinyl chloride, polyolefine (e.g., polyethylene, polypropylene, ethylene-vinylacetate copolymer and the like), polyamide, polyester (e.g., polyethylene terephthalate (PET), polybutylene terephthalate and the like), polyurethane, polystyrene resin, fluoro-based resin (e.g., polytetrafluoroethylene, ethylene-tetrafluoroethylene copolymer and the like), polyimide, and the like; and various elastomers such as polyurethane-based elastomer, polyester-based elastomer, polyolefine-based elastomer, polyamide-based elastomer, polystyrene-based elastomer, fluorine-based elastomer, silicone rubber, fluororubber, latex rubber, and the like. These can be used alone or as a mixture of two or more thereof. In this invention, a material containing at least one of low hardness polyurethane-based elastomer, low hardness polyolefin-based elastomer, and low hardness polyester-based elastomer is preferably used to form the intermediate layer 33, since such elastomers have high elasticity.

Although the intermediate layer 33 in this embodiment is given a single layer construction, it may be given a construction of two or more layers.

In this invention, the average thickness of the intermediate layer 33 is not particularly limited, but the average thickness is preferably in the range of 0.05 to 0.8 mm, and more preferably in the range of 0.05 to 0.4 mm.

X. Eighth Embodiment (Flexible Tube 1H)

Figure 9:
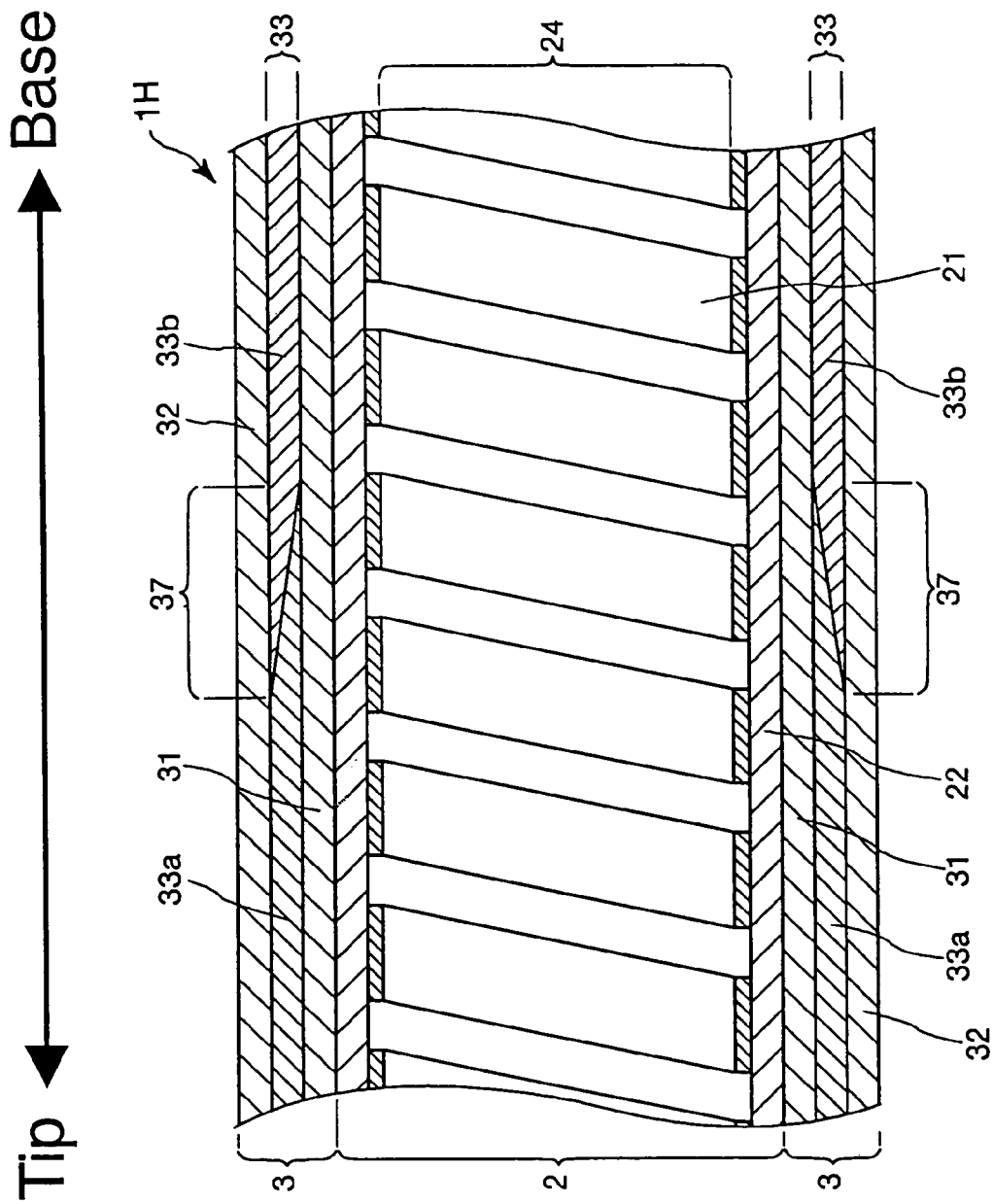
FIG. 9 is a sectional view which shows a part of an eighth embodiment of the flexible tube according to the present invention.

Next, an eighth embodiment of the flexible tube for an endoscope will be described with reference to FIG. 9. FIG. 9 is a sectional view which shows a part of a flexible tube 1H according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1.

As shown in FIG. 9, the outer cover 3 of the flexible tube 1H has a laminate structure composed of inner, outer and intermediate layers 31–33. Each of the inner and outer layers 31 and 32 has a substantially uniform thickness over its entire region, and has almost homogeneous property over its entire region. The intermediate layer 33 has a first portion (first region) 33a formed in a tip side region, and a second portion (second region) 33b formed in a base side region. The first and second portions 33a and 33b of the intermediate layer 33 have different properties. As shown in FIG. 9, the first and second portions 33a and 33b are contiguous to each other through a boundary part (property-varying region) 37 formed between the first and second portions 33a and 33b, and they are arranged along the longitudinal direction. In this invention, it is preferable that the first portion 33a is formed of a material having a lower hardness (stiffness) than that of a material constituting the second portion 33b.

Within the boundary part 37, its property gradually varies in the longitudinal direction. A tip end portion of the boundary part 37 has substantially the same property as that of the first portion 33a, while a base end portion of the boundary part 37 has substantially the same property as that of the second portion 33b.

The boundary part 37 described above is formed through an extrusion molding process. Specifically, a mixture of a constituent material for the first portion 33a and a constituent material for the second portion 33b is prepared first, and then the mixture is fed during the extrusion molding while gradually changing the mixing rate of these materials. In this way, the outer cover 3 which has a layer with a boundary part where its property changes gradually in the longitudinal direction is formed. However, the structure of the boundary part 37 is not limited to that as described above. For example, the boundary part 37 may be formed as a laminated part (composite part) composed of two halves. In this case, a first half is formed of a material having the same property as the first portion 33a such that its thickness gradually decreases in the direction from the tip side to the base side. Further, a second half is formed of a material having the same property as the second portion 33b such that its thickness gradually decreases in the direction from the base side to the tip side.

The length in the longitudinal direction of the boundary part 37 is not particularly limited. For example, when the boundary part 37 is formed so as to have a relatively large length, it is possible give a flexible tube a stiffness which varies more gradually in the longitudinal direction. However, in this invention, the length of the boundary part 37 is preferably in the range of 5 to 600 mm, and more preferable in the range of 10 to 400 mm.

By configuring a flexible tube as described above, it is possible to form an intermediate layer so as to have relatively low stiffness in the first portion 33a located at the tip side, and have relatively high stiffness in the second portion 33b located at the base side. In addition, it is also possible to form the intermediate layer 33 such that a boundary part (property-varying region) 37 where its property varies gradually along the longitudinal direction is formed between the first and second portions 33a and 33b.

According to the flexible tube as described above, due to the formation of the boundary part 37 as well as the homogeneous formation of the inner and outer layers 31 and 32, the stiffness of the flexible tube 1H gradually varies within the boundary part 37 and in the vicinity of its both ends. This structure makes it possible to provide a flexible tube whose stiffness (e.g., bending stiffness) varies more gradually along the longitudinal direction as compared with the flexible tube 1G (FIG. 8) of the seventh embodiment described above. When an endoscope with the flexible tube having the structure as described above is used during an endoscopic examination, it is possible to reduce burden on a patient, since the operator can more safely and smoothly insert the insertion portion of the endoscope into a body cavity of the patient.

Further, according to the flexible tube 1H of this embodiment, there is no spot where the stiffness varies abruptly, since the intermediate layer 33 has the boundary part (property-varying region) 37, and the inner and outer layers 31 and 32 are formed almost homogeneously. Therefore, a push-in force or a rotational force applied by the operator from the base side will not be concentrated at any portion, so that the force can be transmitted sufficiently to the tip end of an endoscope with the flexible tube. In addition, because of the absence of a spot where the stiffness varies abruptly, tendency of the flexible tube to curl or twist will not concentrate at any portion of the flexible tube.

In addition, according to the flexible tube of this embodiment, each of the inner and outer layers 31 and 32 is formed homogeneously over its entire region. This formation makes it possible for the inner layer 31 to have a uniform and high adhesion with the core body 2 over its entire region, and also makes it possible for the outer layer 32 to have uniform and high resistance to chemical over its entire length.

XI. Ninth Embodiment (Flexible Tube 1I)

Figure 10:
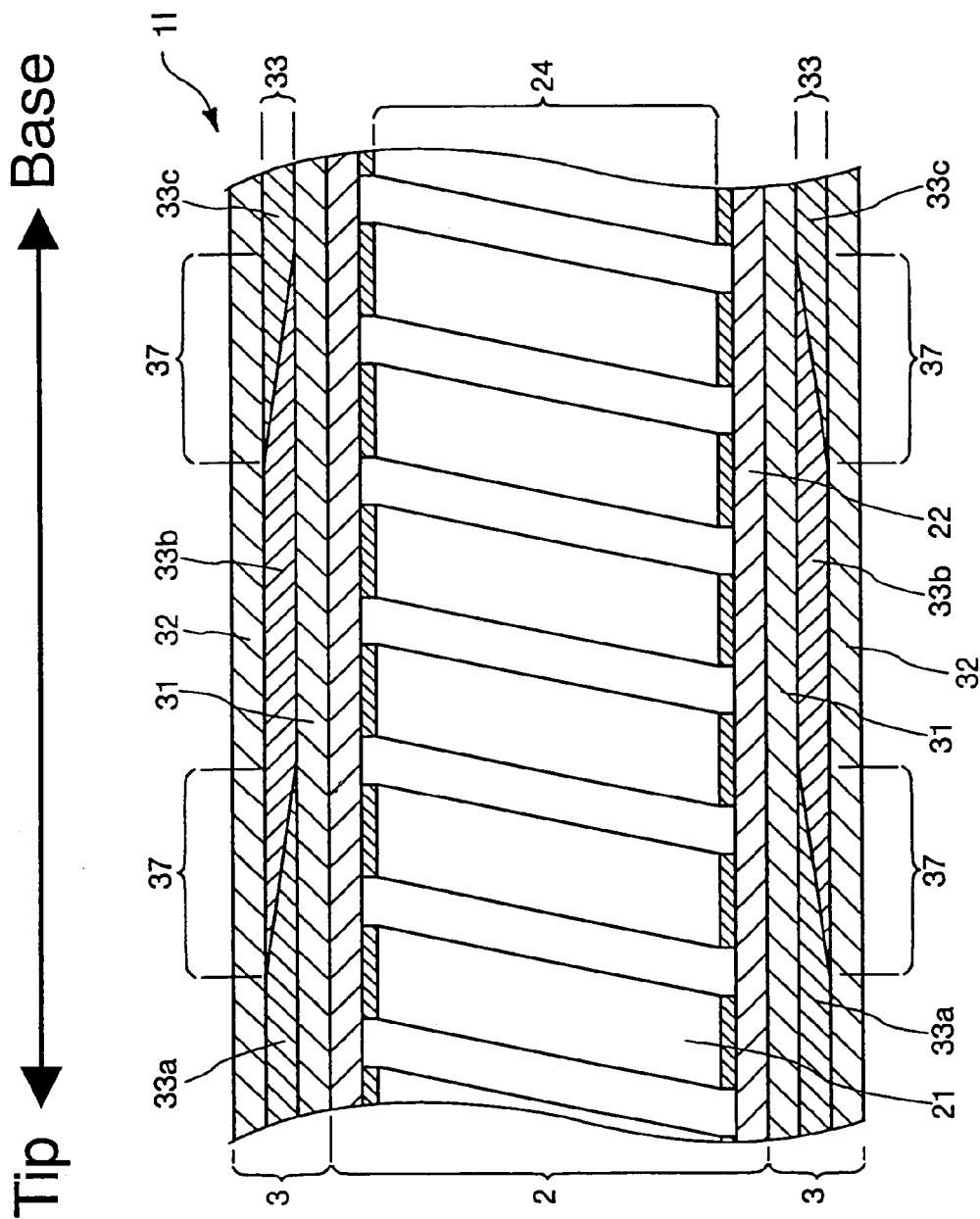
FIG. 10 is a sectional view which shows a part of a ninth embodiment of the flexible tube according to the present invention.

Next, a ninth embodiment of the flexible tube for an endoscope will be described with reference to FIG. 10. FIG. 10 is a sectional view which shows a part of a flexible tube 1I according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1.

As shown in FIG. 10, an outer cover 3 of the flexible tube 1I has a laminate structure composed of inner, outer and intermediate layers 31–33. Each of the inner and outer layers 31 and 32 has a substantially uniform thickness and a substantially homogeneous property over its entire region. The intermediate layer 33 has three distinct portions (i.e., first–third portions 33a–33c). The first portion (first region) 33a is formed at the tip side, the third portion (third region) 33c is formed at the base side, and the second portion (second region) 33b is formed between the first portion 33a and the third portion 33c. Each of the first and third portions 33a and 33c is different from the second portion 33b in its property. In this invention, it is preferable that the first portion 33a is formed of a material having a lower hardness (stiffness) than that of a material constituting the second portion 33b. Further, it is also preferable that the second portion 33b is formed of a material having a lower hardness (stiffness) than that of a material constituting the third portion 33c.

In addition, the intermediate layer 33 has two boundary parts (property-varying regions) 37 which are formed between the first and second portions 33a and 33b and between the second and third portions 33b and 33c, respectively. Each of the boundary parts 37 has substantially the same structure as that of the intermediate layer 33 of the flexible tube 1H (FIG. 9) in the eighth embodiment described above, and formed in the same manner as in the eighth embodiment.

In this embodiment, the length of each of the portions of the intermediate layer 33 is not particularly limited. However, it is preferable that the length of the first portion 33a is preferably in the range of about 50 to 1000 mm, and more preferably in the range of about 100 to 700 mm. Further, it is preferable that the length of the second portion 33b is preferably in the range of about 50 to 800 mm, and more preferably in the range of about 100 to 600 mm. Furthermore, it is preferable that the length of the third portion 33c is preferably in the range of about 50 to 1000 mm, and more preferably in the range of about 200 to 1000 mm.

According to the flexible tube 1I having the structure described above, the intermediate layer 33 has a relatively low stiffness in the first portion 33a located at the tip side, has a relatively high stiffness in the third portion 33c located at the base side, and has a medium stiffness in the second portion 33b between the first and second portions 33a and 33b. In addition, the stiffness of the intermediate layer 33 gradually varies within each of the boundary parts 37 formed between the first and second portions 33a and 33b and between the second and third portions 33b and 33c, respectively.

Further, according to the flexible tube 1I described above, as a result of the formation of the three distinct portions 33a–33c, the stiffness of the flexible tube 1I varies along the longitudinal direction in roughly three stages. In addition, as a result of the formation of the two boundary parts (property-varying regions) 37, the stiffness of the flexible tube 1I varies more gradually along the longitudinal direction. Accordingly, the stiffness of the flexible tube 1I in this embodiment varies along the longitudinal direction in a more gradual manner as compared with the flexible tube 1H (FIG. 9) of the eighth embodiment in which the stiffness varies in roughly "two" stages. Therefore, when an endoscope with the flexible tube 1I having the structure as described above is used during an endoscopic examination, it is possible to reliably reduce burden on a patient, since the operator can more safely and smoothly insert an insertion portion of an endoscope.

XII. Tenth Embodiment (Flexible Tube 1J)

Figure 11:
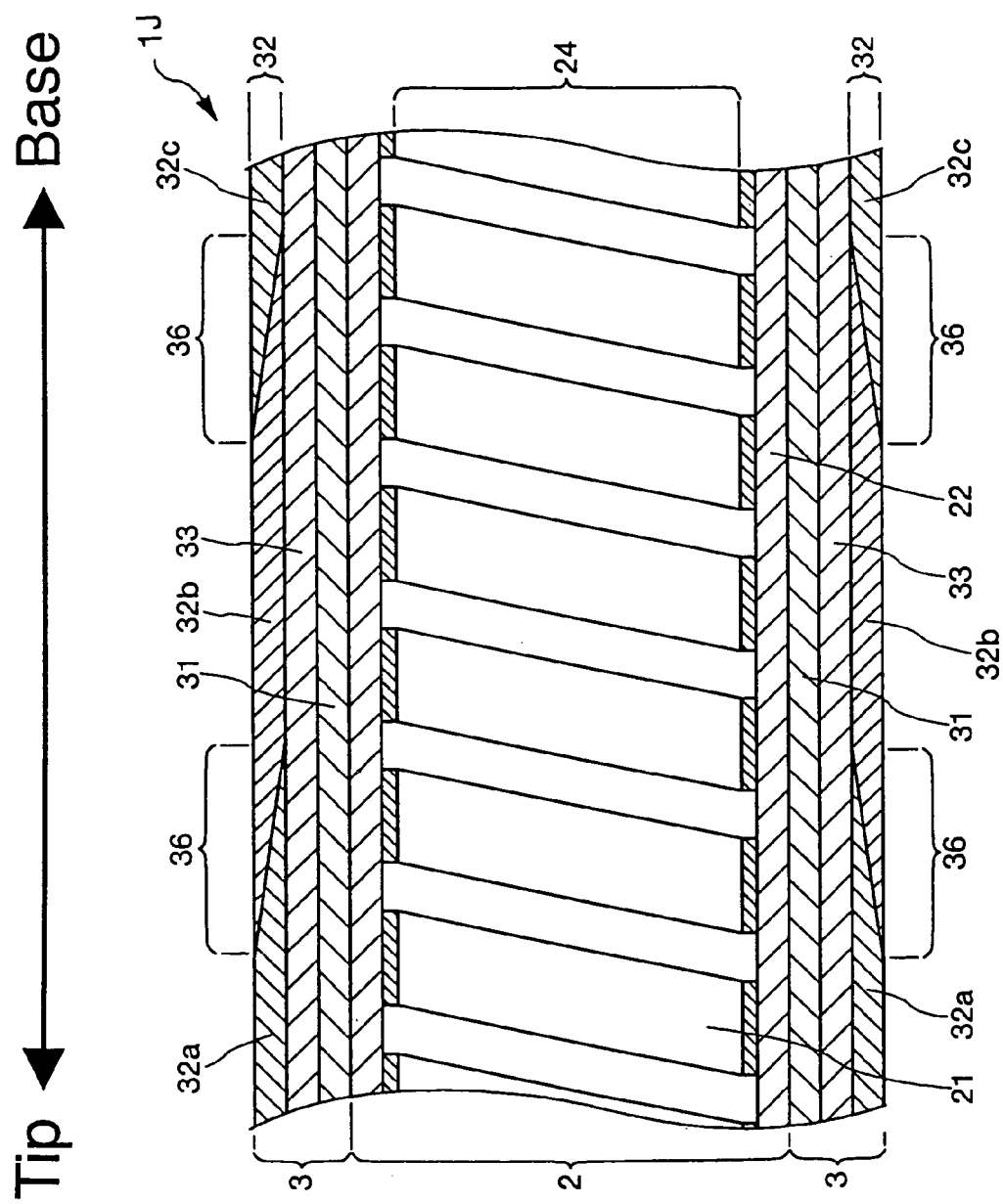
FIG. 11 is a sectional view which shows a part of a tenth embodiment of the flexible tube according to the present invention.

Next, a tenth embodiment of the flexible tube for an endoscope will be described with reference to FIG. 11. FIG. 11 is a sectional view which shows a part of a flexible tube 1J according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1.

As shown in FIG. 11, an outer cover 3 of the flexible tube 1J has a laminate structure composed of inner, outer and intermediate layers 31–33. Each of the inner and intermediate layers 31 and 33 has homogeneous formation and a substantially uniform thickness over its entire region. The outer layer 32 has three distinct portions (i.e., first–third portions 32a–32c). The first portion (first region) 32a is formed at the tip side, the third portion (third region) 32c is formed at the base side, and the second portion (second region) 32b is formed between the first portion 32a and the third portion 32c. Each of the first and third portions 32a and 32c is different from the second portion 32b in its property. In this invention, it is preferable that the first portion 32a is formed of a material having a lower hardness (stiffness) than that of a material constituting the second portion 32b. Further, it is also preferable that the second portion 32b is formed of a material having a lower hardness (stiffness) than that of a material constituting the third portion 32c. In addition, in this invention, it is preferable that each of the first–third portions 32a–32c of the outer layer 32 has high resistance to chemical.

The outer layer 32 has two boundary parts (property-varying regions) 36 which are formed between the first and second portions 32a and 32b and between the second and third portions 32b and 32c, respectively. Each of the boundary parts 36 has substantially the same structure as that of the intermediate layer 33 of the flexible tube 1H (FIG. 9) in the eighth embodiment described above, and formed in the same manner as in the eighth embodiment.

In this embodiment, the length of each of the portions of the outer layer 32 is not particularly limited. However, it is preferable that the length of the first portion 32a is preferably in the range of about 50 to 1000 mm, and more preferably in the range of about 100 to 700 mm. Further, it is preferable that the length of the second portion 32b is preferably in the range of about 50 to 800 mm, and more preferably in the range of about 100 to 600 mm. Furthermore, it is preferable that the length of the third portion 32c is preferably in the range of about 50 to 1000 mm, and more preferably in the range of about 200 to 1000 mm.

In the flexible tube 1J having the structure described above, the outer layer 32 has a relatively low stiffness in the first portion 32a located at the tip side, has a relatively high stiffness in the third portion 32c located at the base side, and has a medium stiffness in the second portion 32b between the first and third portions 32a and 32c. In addition, the stiffness of the outer layer 32 gradually varies within each of the boundary parts (property-varying regions) 36 formed between the first and second portions 32a and 32b and between the second and third portions 32b and 32c, respectively. Therefore, according to the flexible tube 1J described above, it is possible to achieve the same advantages as those described with respect to the flexible tube 1I (FIG. 10) in the ninth embodiment.

In addition, according to the flexible tube 1J of this embodiment, each of the inner and intermediate layers 31 and 33 is formed homogeneously over its entire region. This formation makes it possible for the inner layer 31 to have a uniform and high adhesion with the core body 2 over its entire region, and also makes it possible for the intermediate layer 33 to have uniform and high flexibility over its entire length.

XIII. Eleventh Embodiment (Flexible Tube 1K)

Figure 12:
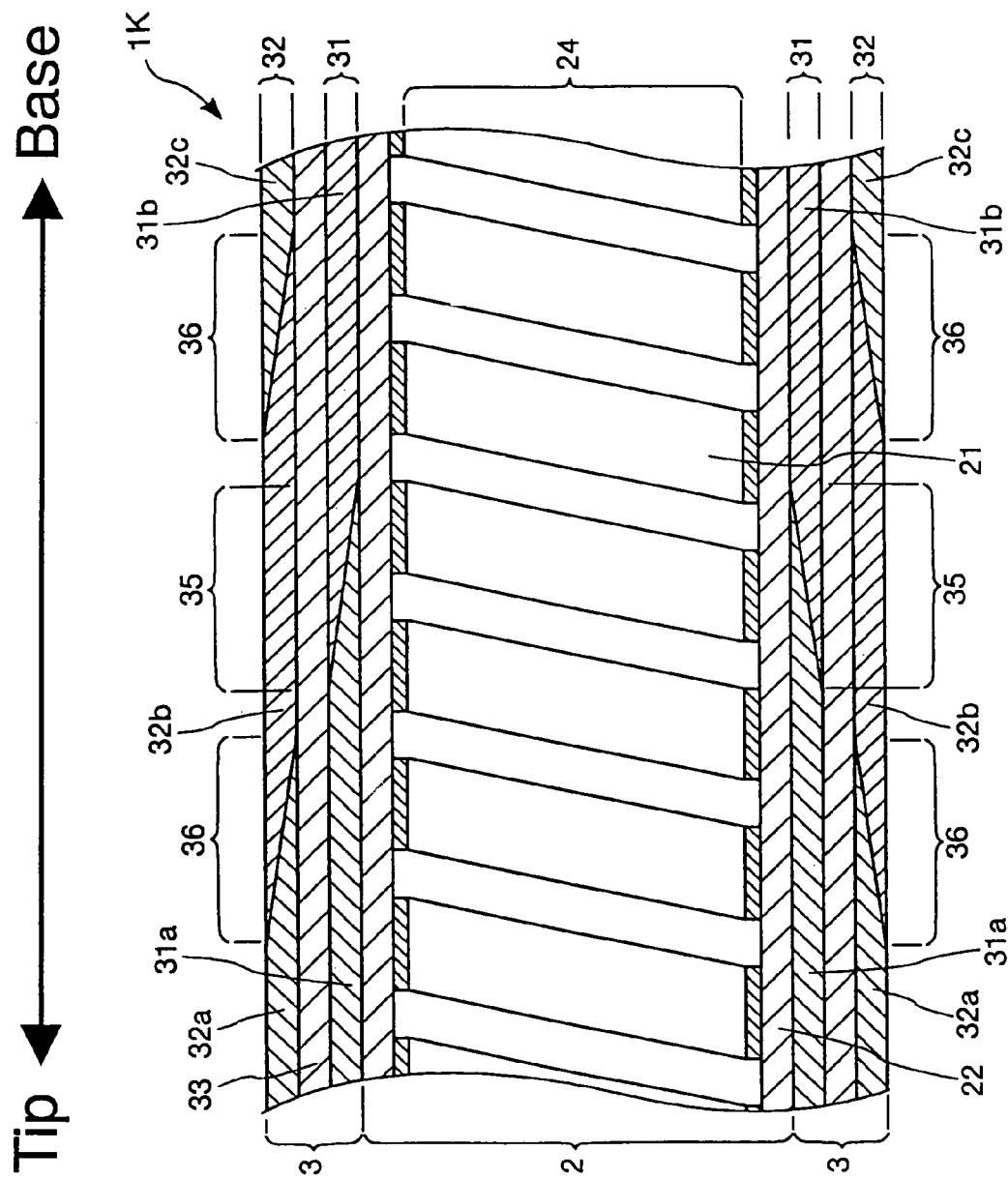
FIG. 12 is a sectional view which shows a part of an eleventh embodiment of the flexible tube according to the present invention.

Next, an eleventh embodiment of the flexible tube for an endoscope will be described with reference to FIG. 12. FIG. 12 is a sectional view which shows a part of a flexible tube 1K according to the present invention, in which illustration of projections 4 as shown in FIG. 2 is omitted, and structure of a reticular tube 22 is simply illustrated as a layer. In this figure, the right-hand side corresponds to the side of the base end 11 shown in FIG. 1 (i.e., side closer to an operator), and the left-hand side corresponds to the side of tip end 12 shown in FIG. 1.

As shown in FIG. 12, an outer cover 3 of the flexible tube 1K has a laminate structure composed of inner, outer and intermediate layers 31–33.

The intermediate layer 33 has a substantially uniform thickness over its entire region, and is formed homogeneously over its entire region.

The outer layer 32 has the same structure as that described with reference to the tenth embodiment shown in FIG. 11. Specifically, the outer layer 32 has three distinct portions (i.e., first–third portions 32a–32c). The first portion (first region) 32a is formed at the tip side, the third portion (third region) 32c is formed at the base side, and the second portion (second region) 32b is formed between the first portion 32a and the third portion 32c. Each of the first and third portions 32a and 32c is different from the second portion 32b in its property. In this invention, it is preferable that the first portion 32a is formed of a material having a lower hardness (stiffness) than that of a material constituting the second portion 32b. Further, it is also preferable that the second portion 32b is formed of a material having a lower hardness (stiffness) than that of a material constituting the third portion 32c. In addition, in this invention, it is preferable that each of the first–third portions 32a–32c of the outer layer 32 has high resistance to chemical.

Further, the outer layer 32 has two boundary parts (property-varying regions) 36 which are formed between the first and second portions 32a and 32b and between the second and third portions 32b and 32c, respectively. Each of the boundary parts 36 has substantially the same structure as that of the intermediate layer 33 of the flexible tube 1H (FIG. 9) in the eighth embodiment described above, and formed in the same manner ass in the eighth embodiment.

The inner layer 31 has two distinct portions (i.e., first and second portions 31a and 31b). The first portion (first region) 31a is formed at the tip side, and the second portion (second region) 31b is formed at the base side. The first portion 31a is different from the second portion 31b in its property. In this invention, it is preferable that the first portion 31a is formed of a material having a lower hardness (stiffness) than that of a material constituting the second portion 31b. Further, it is also preferable that each of the first and second portions 31a and 31b of the inner layer 31 is formed of a material having high adhesion with a core body 2, that is, a material which are easily formed into a layer with projections 4 as shown in FIG. 2 through extrusion molding.

In addition, the inner layer 31 has a boundary part (property-varying region) 35 which is formed between the first and second portions 31a and 31b. The boundary part 35 has substantially the same structure as that of the intermediate layer 33 of the flexible tube 1H (FIG. 9) in the eighth embodiment described above, and formed in the same manner as in the eighth embodiment.

In this embodiment, the length of the first and second portions 31a and 31b of the inner layer 31 is not particularly limited. However, it is preferable that the length of the first portion 31a is preferably in the range of about 50 to 1000 mm, and more preferably in the range of about 500 to 1000 mm. Further, it is preferable that the length of the second portion 31b is preferably in the range of about 50 to 1000 mm, and more preferably in the range of about 400 to 1000 mm.

According to the flexible tube 1K having the structure described above, the outer cover 3 of the flexible tube 1K has different stiffness in the following four regions (1)–(4). (The stiffness of the flexible tube 1K increases in this order in the longitudinal direction.)

(1) A region of the outer cover 3 where both the first portion 32a of the outer layer 32 and the first portion 31a of the inner layer 31 are formed, and where these portions partly face each other.

(2) A region of the outer cover 3 where both the second portion 32b of the outer layer 32 and the first portion 31a of the inner layer 31 are formed, and where these portions partly face each other.

(3) A region of the outer cover 3 where both the second portion 32b of the outer layer 32 and the second portion 31b of the inner layer 31 are formed, and where these portions partly face each other.

(4) A region of the outer cover 3 where both the third portion 32c of the outer layer 32 and the second portion 31b of the inner layer 31 are formed, and where these portions partly face each other.

Therefore, the flexibility of the flexible tube 1K varies along the longitudinal-direction in roughly four stages. Further, as a result of the formation of the boundary parts (property-varying regions) 35 and 36, the stiffness of the flexible tube varies more gradually along the longitudinal direction. Accordingly, the stiffness of the flexible tube 1K in this embodiment varies along the longitudinal direction in a more gradual manner as compared with the flexible tube 1I (FIG. 10) of the ninth embodiment in which the stiffness varies in roughly "three" stages. Therefore, when an endoscope with the flexible tube having the structure as described above is used during an endoscopic examination, it is possible to reliably reduce burden on a patient, since the operator can more safely and smoothly insert the insertion portion of the endoscope into a body cavity of the patient.

Further, according to the flexible tube 1K having the structure described above, the outer cover 3 of the flexible tube 1K is formed such that the boundary part 35 of the inner layer 31 is not located below the boundary parts 36 of the outer layer 32 in the thickness direction. In other words, the outer cover 3 of the flexible tube is formed such that the boundary part 35 of the inner layer 31 and the boundary part 36 of the outer layer 32 are alternately located in the longitudinal direction of the outer cover 3. This arrangement makes it possible for a flexible tube to have a stiffness that varies more gradually in the longitudinal direction.

XIV. Examples of Modification

In the above, the flexible tube for an endoscope according to the present invention was described in detail. However, it is to be noted that this invention is not limited to the embodiments described above.

For example, one or more of layers of the outer cover 3 may be formed using materials which contain the same principal material (main polymer) but which are different in molecular weight, the content of additives (e.g., plasticizer), or the like. Alternatively, one or more of layers of the outer cover 3 may also be formed of materials which contain the same components but which are different in density. In this way, it is also possible to form an outer cover 3 such that a layer of the outer cover 3 has distinct portions having different properties.

Further, the structure of each layer of the outer cover 3 is not particularly limited. For example, an outer cover 32 of a flexible tube may be formed such that any one of layers has regions having different properties. Further, an outer cover of a flexible tube may also be formed such that each of two or more of layers has regions having different properties.

Furthermore, the structure of an outer cover 3 described above is not particularly limited. For example, an outer cover of a flexible tube may be formed such that a part of the outer cover has a laminate structure composed of a plurality of layers.

In addition, for example, the flexible tube for an endoscope according to the present invention may be applied to other site of the endoscope such as a flexible tube for a light guide connected to a light source device.

XV. Examples of Seventh–Eleventh Embodiments

Next, specific examples of the seventh–eleventh embodiments of the present invention will be described below.

1. Preparation of Flexible Tube for an Endoscope

Example 3a

First, a coil 21 having an outer diameter of 9.9 mm and an inner diameter of 9.6 mm was prepared by winding a band-shaped stainless steel material having a width of 3 mm. Next, stainless steel fine wires 23 at least one of which had been given a coating of a polyamide resin and each of which had a diameter of 0.1 mm were prepared, and then using these fine wires a plurality of bundles of ten fine wires were prepared. These bundles of the ten fine wires 23 were woven together in a lattice manner to obtain a reticular tube 22. Then, the obtained reticular tube 22 was provided on the prepared coil 21 so that the outer periphery of the coil 21 was covered with the reticular tube 22. In this way, a core body 2 was prepared.

Next, using an extrusion-molding machine, an outer cover 3 composed of inner, outer and intermediate layers 31–33 was provided on the outer periphery of the core body 2 so that the core body 2 was covered with the outer cover 3. In this way, a flexible tube for an endoscope with a length of 1.6 m was prepared. In this connection, it is to be noted that the length of 1.6 m means the length of an available (effective) portion of the flexible tube that can be used for a flexible tube for an endoscope, that is the length of 1.6 m means an available (effective) length of the flexible tube. Therefore, the actually prepared flexible tube had a length more than 1.6 m by including additional portions at the both ends of the available portion of the flexible tube (See FIG. 14). In this regard, however, it goes without saying that the available length is not limited to 1.6 m mentioned above.

The details of each of the inner, outer and intermediate layers are as follows.

<Inner Layer>
The inner layer 31 was formed so as to have a single region with a uniform thickness. The thickness and a constituent material of the inner layer 31 were as follows.
Thickness: 0.2 mm
Material: A medium hardness polyurethane-based elastomer having a hardness of A81. (Hardness was measured in accordance with JIS K 7311.)

<Outer Layer>
The outer layer 32 was formed so as to have a single region with a uniform thickness. The thickness and a constituent material of the outer layer 32 were as follows.
Thickness: 0.1 mm
Material: A High hardness polyester-based elastomer having a hardness of A92 (Hardness was measured in accordance with JIS K 7311.)

<Intermediate Layer>
The intermediate layer 33 was formed so as to have a uniform thickness (0.3 mm) and to have first, second and third portions 33a–33c. The first portion 33a was formed at the tip side, the second portion 33b was formed between the first and third portions 33a and 33c, and the third portion 33c was formed at the base side. The first portion 33a was contiguous to the second portion 33b through a boundary 34, and the third portion 33c was contiguous to the second portion 33b through a boundary 34. The details of each of the portions 33a–33c are as follows.

--First Portion--
Length: 440 mm
Material: A low hardness polyurethane-based elastomer having a hardness of A68. (Hardness was measured in accordance with JIS K 7311.)

--Second Portion--
Length: 530 mm
Material: A medium hardness polyurethane-based elastomer having a hardness of A82. (Hardness was measured in accordance with JIS K 7311.)

--Third Portion--
Length: 630 mm
Material: A high hardness polyurethane-based elastomer having a hardness of A90. (Hardness was measured in accordance with JIS K 7311.)

Example 3b

A flexible tube for an endoscope was prepared in the same manner as in Example 3a except that the configuration of an intermediate layer 33 was changed as follows.

--First Portion--
Length: 450 mm
Material: A low hardness polyurethane-based elastomer having a hardness of A68. (Hardness was measured in accordance with JIS K 7311.)

--Second Portion--
Length: 300 mm

Material: A medium hardness polyurethane-based elastomer having a hardness of A82. (Hardness was measured in accordance with JIS K 7311.)

--Third Portion--

Length: 450 mm

Material: A high hardness polyurethane-based elastomer having a hardness of A90. (Hardness was measured in accordance with JIS K 7311.)

--Boundary Parts--

In this Example, two boundary parts 37 each of which had a length of 200 mm were formed in the intermediate layer 33. One of the boundary part 37 was formed between the first and second portions 33a and 33b, and the other boundary part 37 was formed between the second and third portions 33b and 33c. Each of the boundary parts 37, was formed through an extrusion molding process so that its property gradually changes in the longitudinal direction. Specifically, first, a mixture of a constituent material for the first portion 33a and a constituent material for the second portion 33b was fed in an extrusion molding machine while gradually changing the mixing rate of these materials. Further, a mixture of a constituent material for the second portion 33b and a constituent material for the third portion 33c was fed in the extrusion molding machine while gradually changing the mixing rate of these materials.

Example 3c

A flexible tube for an endoscope was prepared in the same manner as in Example 3a except that the configuration of each of outer and intermediate layer 32 and 33 was changed as follows.

<Outer Layer>

In this Example, the outer layer 32 was formed so as to have a uniform thickness (0.1 mm), and so as to have three portions (i.e., first, second and third portions 32a–32c) and two boundary parts (property-varying regions) 36. The details of each of the portions 32a–32c and the boundary parts 36 are as follows.

--First Portion--

Length: 450 mm

Material: A low hardness polyolefine-based elastomer having a hardness of A76. (Hardness was measured in accordance with JIS-K 7311.)

--Second Portion--

Length: 300 mm

Material: A medium hardness polyolefine-based elastomer having a hardness of A85. (Hardness was measured in accordance with JIS K 7311.)

--Third Portion--

Length: 450 mm

Material: A high hardness polyolefine-based elastomer having a hardness of A95. (Hardness was measured in accordance with JIS K 7311.)

--Boundary Part-

In this Example, each of the boundary parts 36 had a length of 200 mm. One of the boundary part 36 was formed between the first and second portions 32a and 32b, and the other boundary part 36 was formed between the second and third portions 32b and 32c.

<Intermediate Layer>

In this Example, the intermediate layer 33 was formed so as to have a single region with a uniform thickness (0.3 mm). A constituent material of the intermediate layer 33 was as follows.

Material: A low hardness polyurethane-based elastomer having a hardness of A78. (Hardness was measured in accordance with JIS K 7311.)

Example 3d

A flexible tube for an endoscope was prepared in the same manner as in Example 3c except that the configuration of an inner layer 31 of an outer cover 3 was changed as follows.

In this Example, the inner layer 31 was formed so as to have a uniform thickness (0.2 mm), and so as to have two portions (i.e., first and second portions 31a and 31b) and a boundary part (property-varying region) 35. The details of each of the portions 31a and 31b and the boundary part 35 are as follows.

--First Portion--

Length: 600 mm

Material: A medium hardness polyurethane-based elastomer having a hardness of A82. (Hardness was measured in accordance with JIS K 7311.)

--Second Portion--

Length: 600 mm

Material: A high hardness polyurethane-based elastomer having a hardness of A91. (Hardness was measured in accordance with JIS K 7311.)

--Boundary Parts--

In this Example, the boundary part 35 having a length of 400 mm was formed between the first and second portions 31a and 31b.

Comparative Example 3a

A core body 2 was prepared in the same manner as in Example 3a. Then, using an extrusion-molding machine, an outer cover 3 composed of inner and outer layers 31 and 32 was provided on the outer periphery of the core body 2 so that the core body 2 was covered with the outer cover 3. In this way, a flexible tube for an endoscope with a length of 1.6 m was prepared. The details of each of the layers 31 and 32 of the outer cover 3 are as follows.

<Inner Layer>

The inner layer 31 was formed so as to have a single region with a uniform thickness. The thickness and a constituent material of the inner layer 31 were as follows.

Thickness: 0.3 mm

Material: A medium hardness polyurethane-based elastomer having a hardness of A81. (Hardness was measured in accordance with JIS K 7311.)

<Outer Layer>

The outer layer 32 was formed so as to have a single region with a uniform thickness. The thickness and a constituent material of the outer layer 32 were as follows.

Thickness: 0.3 mm

Material: A low hardness polyurethane-based elastomer having a hardness of A68. (Hardness was measured in accordance with JIS K 7311.)

Comparative Example 3b

A flexible tube for an endoscope was prepared in the same manner as in Comparative Example 3a except that a constituent material for each of inner and outer layers 31 and 32 was changed as follows.

<Inner Layer>

Material: A medium hardness polyurethane-based elastomer having a hardness of A81. (Hardness was measured in accordance with JIS K 7311.)

<Outer Layer>
Material: A high hardness polyester-based elastomer having a hardness of A92. (Hardness was measured in accordance with JIS K 7311.)

Comparative Example 3c

A flexible tube for an endoscope was prepared in the same manner as in Comparative Example 3a except that a constituent material for each of inner and outer layers 31 and 32 was changed as follows.
<Inner Layer>
Material: A high hardness polyurethane-based elastomer having a hardness of A90. (Hardness was measured in accordance with JIS K 7311.)
<Outer Layer>
Material: A high hardness polyester-based elastomer having a hardness of A92. (Hardness was measured in accordance with JIS K 7311.)

2. Observation of the Prepared Flexible Tubes

An observation of the cross-section of the outer cover was carried out for each of the flexible tubes of Examples 3a–3d and Comparative Examples 3a–3c. Through the observation, formation of projections 4 as shown in FIG. 2 was observed in each of the flexible tubes of Examples 3a–3d and Comparative Examples 3a and 3b, but no formation of projections 4 was observed in the flexible tube of Comparative Example 3c.

3. Measurement of Rate of Change in Bending Stiffness

The rate of change in the bending stiffness in the longitudinal direction was measured for each of the flexible tubes of Examples 3a–3d.

Figure 14:
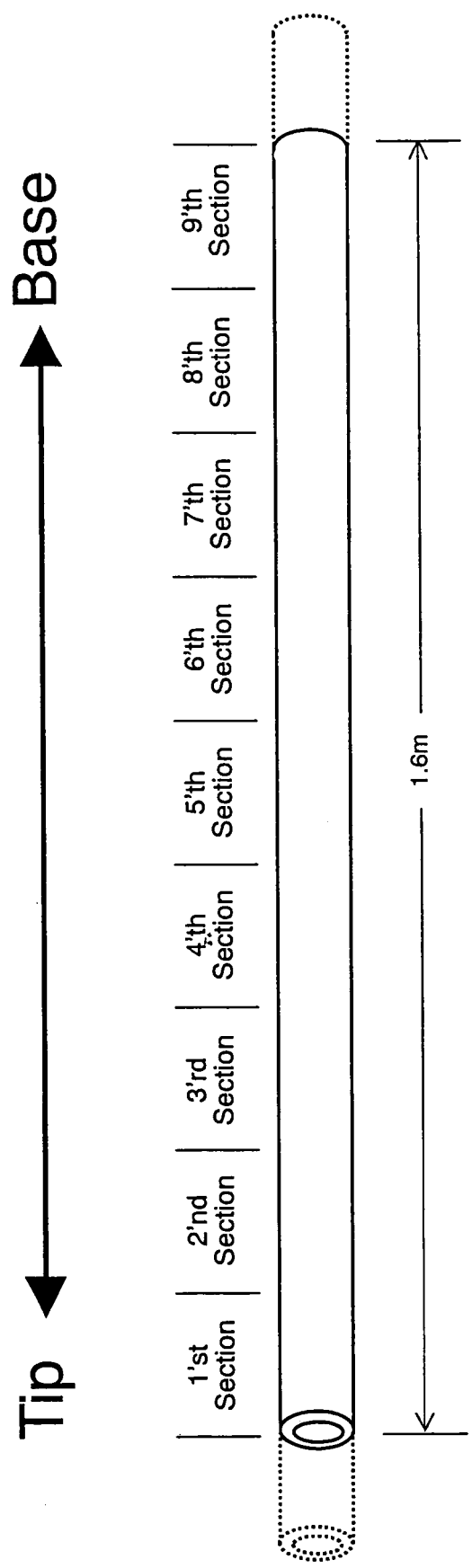
FIG. 14 is an illustration which shows a state where an flexible tube is divided into ninth sections.

For each flexible tube, first the flexible tube was divided into nine sections (i.e., first–ninth sections as shown in FIG. 14) which have an equal length (177 mm) in the longitudinal direction, and then the bending stiffness in "each" of the nine sections of the flexible tube was measured according to the following method.

In the measurement, as shown in FIG. 15, first the flexible tube was laid on two supporting-points located a distance L (177 mm) a part so that both ends of one of the sections were supported by the two supporting-points. Then, the magnitude of the pressing force F when the central point of the section was displaced downward by a predetermined distance y (50 mm) was measured and defined as the bending stiffness of the section. Based on the measured value, the rate of change in the bending stiffness in the longitudinal direction of the flexible tube was calculated. The results of this measurement are shown in the attached Table 5.

4. Evaluation of Flexible Tube (4-1) Insertion (Operationability) Test

An insertion test was carried out for each of the flexible tubes of Examples 3a–3d and Comparative Examples 3a–3c to evaluate operationability of an endoscope with the flexible tube during insertion of the endoscope.

Before carrying out the insertion test, endoscopes as shown in FIG. 1 were prepared using the flexible tubes of Examples 3a–3d and Comparative Examples 3a–3c. Further, a living body model having an internal structure similar to an internal portion of a human body was prepared. Then, each of the prepared endoscopes was inserted into the internal portion of the living body model until its tip end (i.e., tip of an bendable tube 5) reaches a portion corresponding to a large intestine of a human body. In the insertion test, the operationability during insertion of the endoscope was evaluated in accordance with the four rankings A–D given below.
Rank A:
It is possible to perform insertion operation very smoothly. (A flexible tube of an endoscope of Rank A is considered to be best suited for use as a flexible tube for an endoscope.)
Rank B:
It is possible to perform insertion operation smoothly. (A flexible tube of an endoscope of Rank B is considered to be suited for use as a flexible tube for an endoscope.)
Rank C:
It takes a relatively long time to complete insertion operation. (A flexible tube of an endoscope of Rank C is considered to have problems for use as a flexible tube for an endoscope.)
Rank D:
It is difficult to complete insertion operation. (A flexible tube of an endoscope of Rank D is considered to be unsuited for use as a flexible tube for an endoscope.)
The results of the insertion test are shown in the attached Table 6.

(4-2) Chemical Resistance Test

A chemical resistance test was carried out for each of the flexible tubes of Example 3a–3d and Comparative Example 3a–3c. In this test, 100 L of 10% aqueous solution of iodine held at 25° C. was prepared first, and then each of the prepared flexible tubes was immersed in the aqueous solution for 200 hours. Then, the condition of each flexible tube was evaluated in accordance with the four rankings A–D given below.
Rank A:
No Change in the Appearance; and
No Occurrence of Cracks and Blisters in Outer Cover.
Rank B:
Slight Change in the Appearance; and
Occurrence of Blisters at a Few Spots of Outer Cover.
Rank C:
Large Change in the Appearance; and
Occurrence of Blisters at Many Spots of Outer Cover.
Rank D:
Extremely Large Change in the Appearance; and
Occurrence of a Large Number of Cracks and Blisters on Outer Cover.
The evaluation result in this test is shown in the attached Table 6.

(4-3) Durability Test

A durability test was carried out for each of the flexible tubes of Examples 3a–3d and Comparative Examples 3a–3c. In the durability test, each of the flexible tubes was set to a state where the flexible tube was supported at its both ends, and in this state the operation of bending by 90° was repeated 300 times. Then, the degree of change in the flexibility after the repeated operation of bending was examined to evaluate the durability of each flexible tube in accordance with the four rankings A–D given below.
Rank A:
Almost No Change in Flexibility
(A flexible tube of Rank A is considered to have extremely high durability.)
Rank B:
Slight Lowering of Flexibility
(A flexible tube of Rank B is considered to have high durability.)

Rank C:
  Large Lowering of Flexibility
  (A flexible tube of Rank C is considered to have problems in its durability.)
Rank D:
  Extremely Large Lowering of Flexibility; and
  Occurrence of cracks and the like at many spots of the outer cover.
  (A flexible tube of Rank D is considered to be unsuited for use as a flexible tube for an endoscope.)
The result of the durability test is shown in the attached Table 6.

(4-4) Evaluation

The results in the attached Tables 5 and 6 show that the flexible tube according to the present invention (i.e., Examples 3a–3d) has excellent operationability and high chemical resistance as well as high durability. Further, the results in Table 6 also show that conventional flexible tubes (i.e., Comparative Examples 3a–3c) have some drawbacks.

Specifically, the flexible tube of Comparative Example 3a has poor chemical resistance as well as poor operationability. The poor chemical resistance of this flexible tube is considered to result from the fact that the outer layer of the outer cover is made of the material having poor resistance to chemical. Further, the flexible tube of Comparative Example 3b has poor operationability. Furthermore, the flexible tube of Comparative Example 3c has poor durability as well as poor operationability. The poor durability of this flexible tube is considered to result from the fact that projections 4 as shown in FIG. 2 have not been formed on the inner layer 31.

According to the present invention described above, appropriate materials that are suitable for each of layers of an outer cover are used for preparing the outer cover, and the outer cover is provided onto the core body so that each of the layers has appropriate thickness and shape. This structure and the selection of material make it possible to produce a flexible tube for an endoscope that has high durability, high flexibility and high chemical resistance as well as excellent operationability.

Further, according to the present invention, at least one of layers of an outer cover 3 has at least two distinct portions and a boundary part along its longitudinal direction, and one of the portions is contiguous to the other portion through the boundary part. In this layer, one of the portions is different from the other portion adjacent thereto in physical property or chemical property. This configuration makes it possible for a flexible tube to have a stiffness (flexibility) which gradually varies in its longitudinal direction.

According to an endoscope having the flexible tube as described above, since the flexible tube has a higher stiffness in a portion closer to the base end, it is possible to fully transmit to the tip end of the endoscope the push-in force and the rotational force applied by an operator. On the other hand, since the flexible tube has a higher flexibility in a portion closer to the tip end, it is also possible to smoothly insert an insertion section (flexible tube) of the endoscope into an internal curved portion of a patient in a safe manner. Therefore, the flexible tube as described above makes it possible for an operator to insert the insertion section with easy manipulation, thus enabling the reduction of the burden on the patient during the endoscopic examination.

Furthermore, according to the present invention, a material having high elasticity is used as a constituent material for an intermediate layer of the outer cover. This makes it possible to give high flexibility to a flexible tube.

Moreover, according to the present invention, a material having high chemical resistance is used as a constituent material for an outer layer of the outer cover. This makes it possible to give high chemical resistance to a flexible tube.

In addition, according to the present invention, a material having a high adhesion with a core body is used as a constituent material for an inner layer of the outer cover. This makes it possible to give high durability to a flexible tube.

Finally, it is to be understood that many changes and additions may be made to the embodiments described above without departing from the scope and spirit of the invention as defined in the appended Claims.

Further, it is also to be understood that the present disclosure relates to subject matter contained in Japanese Patent Application Nos. 2000-134922, 2000-142206 and 2000-156783 (filed on May 8, 15 and 26, 2000, respectively) which are expressly incorporated herein by reference in its entirety.

TABLE 1

|  | Inner Layer | | Intermediate Layer | | Outer Layer | | Chemical Resistance | Flexibility | Durability |
| --- | --- | --- | --- | --- | --- | --- | --- | --- | --- |
|  | Material* | Thickness [mm] | Material* | Thickness [mm] | Material* | Thickness [mm] | | | |
| Ex. 1a | M | 0.3 | L | 0.2 | H1 | 0.1 | A | A | A |
| Ex. 1b | M | 0.2 | L | 0.2 | H1 | 0.1 | A | A | A |
| Ex. 1c | M | 0.3 | L | 0.1 | H1 | 0.1 | A | A | A |
| Ex. 1d | M | 0.3 | L | 0.2 | H2 | 0.05 | A | A | A |
| Ex. 1e | M | 0.3 | L | 0.2 | H3 | 0.1 | A | A | A |
| Co. Ex. 1a | M | 0.3 | — | — | L | 0.2 | D | C | B |
| Co. Ex. 1b | M | 0.3 | — | — | H1 | 0.2 | A | D | B |
| Co. Ex. 1c | H1 | 0.2 | — | — | M | 0.3 | C | D | D |
| Co. Ex. 1d | L | 0.3 | — | — | H1 | 0.2 | A | C | D |

Material M: Medium Hardness Polyurethane-Based Elastomer (Hardness*: 81)
Material L: Low Hardness Polyurethane-Based Elastomer (Hardness*: 68)
Material H1: High Hardness Polyester-Based Elastomer (Hardness*: 92)
Material H2: High Hardness Polyolefine-Based Elastomer (Hardness*: 91)
Material H3: High Hardness Polyurethane-Based Elastomer (Hardness*: 92)
*Hardness of the material was measured in accordance with JIS K 7311.

TABLE 2

|  | Inner Layer | Intermediate Layer | Outer Layer |
| --- | --- | --- | --- |
| Example 2a | Material M | Material L | Material H1 |
| Example 2b | Material M | Material L | Material H1 |
| Example 2c | Material M | Material L | Material H1 |
| Example 2d | Material M | Material L | Material H2 |
| Example 2e | Material M | Material L | Material H3 |
| Co. Example 2a | Material M | — | Material L |
| Co. Example 2b | Material M | — | Material H1 |
| Co. Example 2c | Material H1 | — | Material H2 |

Material M: Medium Hardness Polyurethane-Based Elastomer (Hardness*: 81)
Material L: Low Hardness Polyurethane-Based Elastomer (Hardness*: 68)
Material H1: High Hardness Polyester-Based Elastomer (Hardness*: 92)
Material H2: High Hardness Polyolefine-Based Elastomer (Hardness*: 91)
Material H3: High Hardness Polyurethane-Based Elastomer (Hardness*: 92)
*Hardness of the material was measured in accordance with JIS K 7311.

TABLE 3

|  | First Section | Second Section | Third Section | Fourth Section | Fifth Section | Sixth Section | Seventh Section | Eighth Section |
| --- | --- | --- | --- | --- | --- | --- | --- | --- |
| Example 2a | 1 | 1.1 | 1.3 | 1.4 | 1.5 | 1.6 | 1.8 | 1.9 |
| Example 2b | 1 | 1.2 | 1.4 | 1.6 | 1.8 | 1.9 | 2.1 | 2.3 |
| Example 2c | 1 | 1 | 1.5 | 1.5 | 1.8 | 1.8 | 2.2 | 2.2 |
| Example 2d | 1 | 1.3 | 1.5 | 1.7 | 1.9 | 2.1 | 2.3 | 2.4 |
| Example 2e | 1 | 1.1 | 1.3 | 1.4 | 1.5 | 1.6 | 1.8 | 1.9 |

TABLE 4

|  | Operationability | Chemical Resistance | Durability |
| --- | --- | --- | --- |
| Example 2a | A | A | A |
| Example 2b | A | A | A |
| Example 2c | A | A | A |
| Example 2d | A | A | A |
| Example 2e | A | A | A |
| Co. Example 2a | C | D | B |
| Co. Example 2b | D | A | B |
| Co. Example 2c | D | A | D |

TABLE 5

|  | First Section | Second Section | Third Section | Fourth Section | Fifth Section | Sixth Section | Seventh Section | Eighth Section | Ninth Section |
| --- | --- | --- | --- | --- | --- | --- | --- | --- | --- |
| Example 3a | 1 | 1.02 | 1.2 | 1.2 | 1.2 | 1.4 | 1.4 | 1.4 | 1.4 |
| Example 3b | 1 | 1.04 | 1.11 | 1.2 | 1.2 | 1.3 | 1.38 | 1.39 | 1.4 |
| Example 3c | 1 | 1.03 | 1.08 | 1.17 | 1.18 | 1.26 | 1.35 | 1.36 | 1.38 |
| Example 3d | 1 | 1.06 | 1.12 | 1.19 | 1.27 | 1.34 | 1.38 | 1.4 | 1.42 |

TABLE 6

|  | Operationability | Chemical Resistance | Durability |
|---|---|---|---|
| Example 3a | A | A | A |
| Example 3b | A | A | A |
| Example 3c | A | A | A |
| Example 3d | A | A | A |
| Co. Example 3a | C | D | B |
| Co. Example 3b | D | A | B |
| Co. Example 3c | D | A | D |

What is claimed is:

1. A flexible tube for an endoscope, comprising:
an elongated tubular core body; and
an outer cover which is provided over the core body, the outer cover having a portion which is formed into a laminate structure composed of at least three layers, wherein at least one of the layers constituting the portion of the laminate structure has a thickness-varying region where the thickness of the layer varies in its longitudinal direction,
wherein the thickness-varying region extends substantially over an entire region of the layer, and within the thickness-varying region the thickness of the layer varies in its longitudinal direction in a stepwise manner including multiple steps.

2. The flexible tube as claimed in claim 1, wherein the layer with the thickness-varying region has at least one uniform thickness region which is formed so as to adjoin the thickness-varying region.

3. The flexible tube as claimed in claim 1, wherein the layer having the thickness-varying region is formed of a material that is different from materials constituting the other layers in its hardness.

4. The flexible tube as claimed in claim 1, wherein each of at least two of the layers constituting the portion of the laminate structure has a thickness-varying region where the thickness of the layer varies in its longitudinal direction.

5. The flexible tube as claimed in claim 1, wherein the outer cover is provided over the core body through an extrusion molding process.

6. The flexible tube as claimed in claim 5, wherein in the extrusion molding process a constituent material for each of the layers is fed at a predetermined feeding rate while the core body is fed at a predetermined feeding speed, in which the thickness of the layer having the thickness-varying region is controlled by adjusting the feeding rate of the material for the layer during the extrusion molding process and/or adjusting the feeding speed of the core body during the extrusion molding process.

7. The flexible tube as claimed in claim 1, wherein the thickness-varying region varies in thickness in four steps along its longitudinal direction.

8. The flexible tube as claimed in claim 1, wherein the layer having the thickness-varying region comprises:
a thinnest region extending through a first quarter of the layer, which is provided toward an end tip thereof; and
a thickest region extending through a fourth quarter of the layer, which is provided toward a base end thereof.

9. The flexible tube as claimed in claim 8, wherein a thickness ratio of the thinnest region over the thickest region is 0.125.

10. The flexible tube as claimed in claim 8, wherein the thinnest region is 0.05 mm in thickness, and the thickest region is 0.4 mm in thickness.

11. The flexible tube as claimed in claim 1, wherein an intermediate layer varies in thickness in four steps along its longitudinal direction.

12. The flexible tube as claimed in claim 1, wherein an intermediate layer comprises:
a thickest region extending through a first quarter of the layer, which is provided toward an end tip thereof; and
a thinnest region extending through a fourth quarter of the layer, which is provided toward a base end thereof.

13. The flexible tube as claimed in claim 12, wherein a thickness ratio of the thinnest region over the thickest region is 0.125.

14. The flexible tube as claimed in claim 12, wherein the thinnest region is 0.05 mm in thickness, and the thickest region is 0.4 mm in thickness.

15. A flexible tube for an endoscope, comprising:
an elongated tubular core body; and
an outer cover which is provided over the core body, the outer cover having a portion which is formed into a laminate structure composed of at least three layers, wherein at least one of the layers constituting the portion of the laminate structure has at least three regions and at least two boundary parts along its longitudinal direction, and one of the regions is contiguous to the other region through one of the boundary parts, in which one of the regions is different from the other regions adjacent thereto in its physical property and/or chemical property,
wherein each of the boundary parts is formed as a property-varying part within which the physical property and/or the chemical property of the layer gradually vary in its longitudinal direction.

16. The flexible tube as claimed in claim 15, wherein one of the regions is formed of a material which is different from that forming the other region adjacent thereto.

17. The flexible tube as claimed in claim 15, wherein each of at least two of the layers constituting the portion of the laminate structure has at least two regions and at least one boundary part along its longitudinal direction, and one of the regions is contiguous to the other region through the boundary part, in which one of the regions is different from the other region adjacent thereto in its physical property and/or chemical property.

18. The flexible tube as claimed in claim 17, wherein the outer cover is formed such that the boundary part of one layer is not located above or below the boundary part of the other layer in its thickness direction.

19. The flexible tube as claimed in claim 15, wherein the boundary part is formed of a mixture of a material constituting one of the regions and a material constituting the other region.

20. The flexible tube as claimed in claim 15, wherein in the layer having the at least three regions, one of the regions is different from the other region adjacent thereto in its hardness.

21. The flexible tube as claimed in claim 15, wherein the flexible tube has tip and base ends, and flexibility of the flexible tube increases in a gradual or stepwise manner along the direction from the base end to the tip end.

22. The flexible tube as claimed in claim 15, wherein the layers of the laminate structure include an inner layer, an outer layer and at least one intermediate layer formed between the inner layer and the outer layer, and wherein the intermediate layer of the outer cover has a higher elasticity than the inner and outer layers so that the intermediate layer functions as cushioning between the inner layer and the outer layer.

23. The flexible tube as claimed in claim 15, wherein at least one of the layers constituting the portion of the laminate structure has a thickness-varying region where the thickness of the layer varies in its longitudinal direction.

24. A flexible tube for an endoscope, comprising:
  an elongated tubular core body; and
  an outer cover which is provided over the core body, the outer cover having a portion which is formed into a laminate structure composed of at least three layers, wherein at least one of the layers constituting the portion of the laminate structure has at least three regions and at least two boundary parts along its longitudinal direction, and one of the regions is contiguous to the other region through one of the boundary parts, in which one of the regions is different from the other regions adjacent thereto in its physical property and/or chemical property,
  wherein the layer having the boundary parts is formed such that the physical property and/or the chemical property within each of the boundary parts vary in its longitudinal direction in a substantially stepwise manner.

25. The flexible tube as claimed in claim 24, wherein the layers of the laminate structure include an inner layer, an outer layer and at least one intermediate layer formed between the inner layer and the outer layer, and wherein the intermediate layer of the outer cover has a higher elasticity than the inner and outer layers so that the intermediate layer functions as cushioning between the inner layer and the outer layer.

* * * * *